(12) United States Patent
Runyon et al.

(10) Patent No.: US 11,220,526 B2
(45) Date of Patent: Jan. 11, 2022

(54) NEUROPEPTIDE S RECEPTOR (NPSR) AGONISTS

(71) Applicants: Research Triangle Institute, Research Triangle Park, NC (US); The Regents of the University of California, Oakland, CA (US)

(72) Inventors: Scott Runyon, Hillsborough, NC (US); Danni Harris, Boonville, CA (US); Rainer Reinscheid, Irvine, CA (US); Yanyan Zhang, Morrisville, NC (US); Carla Hassler, Durham, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

(21) Appl. No.: 16/090,728

(22) PCT Filed: Mar. 23, 2017

(86) PCT No.: PCT/US2017/023749
§ 371 (c)(1),
(2) Date: Oct. 2, 2018

(87) PCT Pub. No.: WO2017/176460
PCT Pub. Date: Oct. 12, 2017

(65) Prior Publication Data
US 2019/0127419 A1 May 2, 2019

Related U.S. Application Data

(60) Provisional application No. 62/318,015, filed on Apr. 4, 2016.

(51) Int. Cl.
| | |
|---|---|
| C07K 5/068 | (2006.01) |
| A61K 38/00 | (2006.01) |
| C07K 5/083 | (2006.01) |
| C07K 5/087 | (2006.01) |
| C07K 5/097 | (2006.01) |
| C07K 5/08 | (2006.01) |
| C07K 5/103 | (2006.01) |
| C07K 7/06 | (2006.01) |
| C07K 5/107 | (2006.01) |
| A61P 25/28 | (2006.01) |
| A61P 25/30 | (2006.01) |
| A61P 3/04 | (2006.01) |
| A61P 25/18 | (2006.01) |

(52) U.S. Cl.
CPC .......... *C07K 5/06086* (2013.01); *A61K 38/00* (2013.01); *A61P 3/04* (2018.01); *A61P 25/18* (2018.01); *A61P 25/28* (2018.01); *A61P 25/30* (2018.01); *C07K 5/0804* (2013.01); *C07K 5/0812* (2013.01); *C07K 5/0821* (2013.01); *C07K 5/0827* (2013.01); *C07K 5/101* (2013.01); *C07K 5/1016* (2013.01); *C07K 7/06* (2013.01)

(58) Field of Classification Search
None
See application file for complete search history.

(56) References Cited

U.S. PATENT DOCUMENTS

2011/0312997 A1  12/2011  Wang et al.

FOREIGN PATENT DOCUMENTS

| CN | 101519431 A | 9/2009 |
|---|---|---|
| WO | 2013132317 A1 | 9/2013 |

OTHER PUBLICATIONS

Poleto "Aromatic Rings Commonly Used in Medicinal Chemistry: Force Fields Comparison and Interactions With Water Toward the Design of New chemical entities" Front Pharma 9(395):1-20 (Year: 2018).*
Vitaku "Analysis of the structural diversity, substitution patterns, and frequency of nitrogen heterocycles among U.S. FDA approved pharmaceuticals" J med chem 57(24):10257-74 (abstract only) (Year: 2014).*
Kirsch "BMP-2 antagonists emerge from alterations in the low-affinity binding epitope for receptor BMPR-II" EMBO 19(13):3314-3324 (Year: 2000).*
Cohen "Neuropeptide S in the basolateral amygdala mediates an adaptive behavioral stress response in a rat model of posttraumatic stress disorder by increasing the expression of BDNF and the neuropeptide YY1 receptor" Euro neuro psy pharma 28:159-170 (Year: 2018).*
Zhao "Neuropeptide S Ameliorates Cognitive Impairment of APP/PS1 Transgenic Mice by Promoting Synaptic Plasticity and Reducing Ab deposition" front behav neuro 13(138):1-10 (Year: 2019).*
Zhang "Drug metabolism in drug discovery and development" acta pharma sinica b 8(5):721-732 (Year: 2018).*

(Continued)

*Primary Examiner* — Adam Weidner
(74) *Attorney, Agent, or Firm* — Barnes & Thornburg LLP

(57) ABSTRACT

Neuropeptide S receptor agonists are provided. The NPS agonists include trimeric, tetrameric, pentameric or hexameric peptidomimetic analogs exhibiting affinity for and activity at the neuropeptide S receptor. The peptidomimetic molecules may be useful in the treatment of disorders, syndromes and conditions mediated by modulation of the neuropeptide S receptor such as substance abuse, narcolepsy, insomnia, obesity, cognitive decline, dementia, Alzheimer's disease, panic disorder, generalized anxiety, PTSD, phobias, schizophrenia and as supportive medication during any kind of cessation program in cognitive behavioral therapy, such as drug addiction, eating disorders and gambling.

5 Claims, 7 Drawing Sheets
Specification includes a Sequence Listing.

(56) References Cited

OTHER PUBLICATIONS

Wikipedia "Sterotypy" accessed from wikipedia.org on Jul. 25, 2019 (Year: 2019).*
Watt "Repetitive and Stereotyped Behaviors in Children with Autism Spectrum Disorders in the Second Year of Life" J autism Dev disord 38(8): 1518-1533 (Year: 2008).*
International Search Report dated Nov. 27, 2017 for International Application No. PCT/US2017/023749 filed Mar. 23, 2017.
International Preliminary Report on Patentability dated Oct. 18, 2018 for International Application No. PCT/US2017/023749 filed Mar. 23, 2017.
Behnam et al., "C-Terminal Residue Optimization and Fragment Merging: Discovery of a Potent Peptide-Hybrid Inhibitor of Dengue Protease," ACS Med. Chem. Lett., 2014, vol. 5, No. 9, pp. 1037-1042.
Bernier et al., "Structure-function relationships in the neuropeptide S receptor: molecular consequences of the asthma-associated mutation N107I," J. Biol. Chem., 2006, vol. 281, No. 34, pp. 24704-24712.
Camarda et al., "Structure-activity study at positions 3 and 4 of human neuropeptide S," Biog. & Med. Chem., 2008, vol. 16, No. 19, pp. 8841-8845.
Camarda et al., "Synthesis and Biological Activity of Human Neuropeptide S Analogues Modified in Position 2," J. Med Chem., 2008, vol. 51, No. 3, pp. 655-658.
Chemical Abstract Registration No. 183127-81-3 entered Nov. 14, 1996.
Elphick, "NG Peptides: A Novel Family of Neurophysin-Associated Neuropeptides," Gene, 2010, vol. 458, pp. 20-26.
Guerrini et al., "Synthesis and Biological Activity of Human Neuropeptide S Analogues Modified in Position 5: Identification of Potent and Pure Neuropeptide S Receptor Antagonists," J. Med. Chem., 2009, vol. 52, pp. 524-529.
Myslinski et al., "Protein-Ligand Interactions: Thermodynamic Effects Associated with Increasing the Length of an Alkyl Chain," ACS Med. Chem. Lett., 2013, vol. 4, No. 11, pp. 1048-1053.
Roth et al., J. Biol. Chem., "Structure-activity studies on neuropeptide S: identification of the amino acid residues crucial for receptor activation," 2006, vol. 281, No. 30, pp. 20809-20816.
Jungling, K., et al., "Neuropeptide S-mediated control of fear expression and extinction: role of intercalated GABAergic neurons in the amygdala", Neuron (Jul. 31, 2008), vol. 59, No. 2, pp. 298-310.
Lennertz, L., et al., "The functional coding variant Asn107Ile of the neuropeptides receptor gene (NPSR1) is associated with schizophrenia and modulates verbal memory and the acoustic startle response", International Journal of Neuropsychopharmacology (2012), vol. 15, pp. 1205-1215.
Okamura, N., et al., "Neuropeptide S enhances memory during the consolidation phase and interacts with Noradrenergic systems in the brain", Neuropsychopharmacology (2011), vol. 36, pp. 744-752.
Okamura, N., et al., "Gender-specific association of a functional coding polymorphism in the neuropeptide S receptor gene with panic disorder but not with schizophrenia or attention-deficit/hyperactivity disorder", Progress in Neuro-Psychopharmacology & Biological Psychiatry, (2007), vol. 31, pp. 1444-1448.
Si, W., et al., "Neuropeptide S stimujlates dopaminergic neurotransmission in the medial prefrontal cortex", J. Neurochem. (Oct. 2010), vol. 115, No. 2, pp. 475-482.
Xu, Y-L., et al., "Neuropeptide S: A neuropeptide promoting arousal and anxiolytic-like effects", Neuron, (Aug. 19, 2004), vol. 43, pp. 487-497.

* cited by examiner

Dose response EC50 curves for compounds R06039-351, 354, and 456

SEQUENCE LISTING

```
<160> NUMBER OF SEQ ID NOS: 1

<210> SEQ ID NO 1
<211> LENGTH: 20
<212> TYPE: PRT
<213> ORGANISM: Human

<400> SEQUENCE: 1

Ser Phe Arg Asn Gly Val Gly Thr Gly Met Lys Lys Thr Ser Phe Gln
1               5                   10                  15

Arg Ala Lys Ser
            20
```

NEUROPEPTIDE S RECEPTOR (NPSR) AGONISTS

CROSS-REFERENCE TO RELATED APPLICATIONS

This application is a National Stage application of International Application No. PCT/US2017/023749 filed Mar. 23, 2017, which claims benefit of priority to U.S. Provisional Application No. 62/318,015 filed Apr. 4, 2016. The disclosure of each related application is hereby incorporated herein by reference in its entirety.

GOVERNMENT RIGHTS IN THE INVENTION

This invention was made with government support under Grant No. R01MH087826 awarded by National Institute of Health. The government has certain rights in the invention.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "15844-25_2018-10-02_Sequence_Listing.txt" created on Sep. 28, 2018, and is 4,096 bytes in size. The sequence listing contained in this .txt file is part of the specification and is hereby incorporated by reference herein in its entirety.

FIELD

The present disclosure relates to peptidomimetics that are specific for the neuropeptide S receptor, and which may be used in the treatment of a variety of diseases, syndromes and conditions. The present disclosure further relates to methods, compounds and compositions for selectively modulating the function of neuropeptide S receptors to provide pharmacotherapies capable of influencing conditions or disorders affected by the neuropeptide receptors.

DESCRIPTION OF THE RELATED ART

Neuropeptide S (NPS) is the endogenous ligand for the previous orphan G-protein-coupled receptor GPR154, now referred to as the neuropeptide S receptor (NPSR). Neuropeptide S is a 20-amino acid peptide that functions as an agonist through activation of its cognate $G_q$ or $G_s$ coupled, GPCR receptor system.

By way of selective neuropeptide S receptor activation, neuropeptide S regulates several biological functions including wakefulness, stress and anxiety, locomotor activity, food intake, memory processes, and drug abuse.

In view of the biological activity believed to be affected by NPS, the art is seeking compounds and compositions which provide activation of the desirable effects of NPS.

SUMMARY

The present disclosure relates to neuropeptide S (NPS) peptidomimetic compound according to Formulas IA-ID, Formulas IIA-IIE, Formula III or Formula IV:

(i) tetrameric NPS peptidomimetic compounds IA-ID

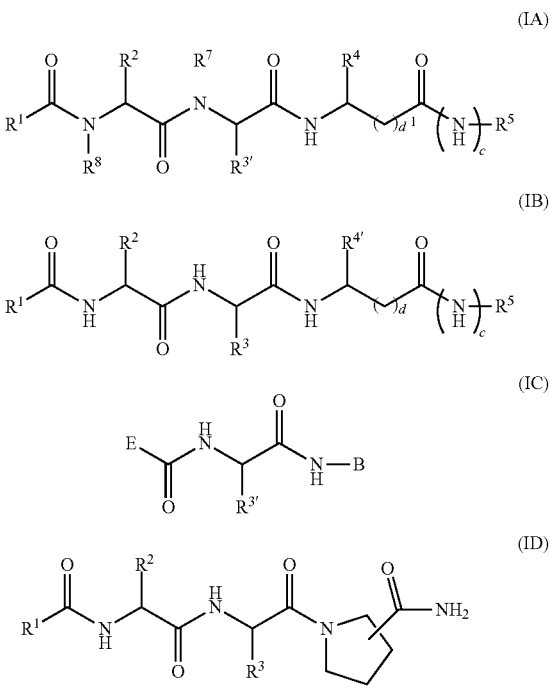

wherein $R^1$ is $CH(NHCH_3)CH_2OH$, $CH(NH_2)(CH_2)_2CH_3$, $CH(NH_2)CH_2OCH_3$, $CH_2CH_2OH$, $NHCH_2CH_3$, $CH(NH_2)CH_2OH$, $CH_2CH_2OCH_3$, branched or unbranched $C_1$-$C_6$ alkyl, heterocycle, heteroaryl, $C_1$-$C_4$ aralkyl, cycloalkyl, or aryl optionally substituted with halo, alkoxy, amino or alkoxyaminoalkyl;

$R^2$ is H, phenylalanine side chain, alkylcycloalkyl, unbranched $C_1$-$C_6$ alkyl, or benzyl substituted with nitro or halo;

$R^3$ is arginine side chain or lysine side chain;

$R^{3'}$ is H, lysine side chain, $C_1$-$C_3$ alkylated or benzylated lysine side chain, alanine side chain, unbranched $C_1$-$C_6$ alkyl, $(CH_2)_4NHCOCF_3$, or benzyl optionally substituted with nitro;

$R^4$ is asparagine side chain or $C_1$-$C_3$ alkyl;

$R^{4'}$ is H, asparagine side chain, $C_1$-$C_3$ alkyl heteroaryl, $C_1$-$C_6$ alkyl, $CH_2OH$, $CH_2CONHCH_3$, $CH_2COOCH_3$, $CH_2CN$;

$R^5$ is H, OH, unbranched $C_1$-$C_6$ alkyl or $C_1$-$C_4$ alkylcycloalkyl;

c is 0 when $R^5$ is OH, or c is 1 when $R^5$ is hydrogen, unbranched $C_1$-$C_6$ alkyl or $C_1$-$C_4$ alkylcycloalkyl;

$R^7$ is H or a lysine side chain, provided that when $R^7$ is a lysine side chain, $R^3$ is H;

$R^8$ is H or $CH_3$;

d is 0 or, when $R^{4'}$ is H, d is 1, or when $R^{4'}$ is $CH_3$, d may be 0 or 1;

$d^1$ is 0 or, when $R^4$ is $CH_3$, $d^1$ is 1;

B is a five membered saturated ring substituted with one $C(O)NH_2$ group or a six membered saturated or aromatic ring substituted with one $C(O)NH_2$ group; and E is

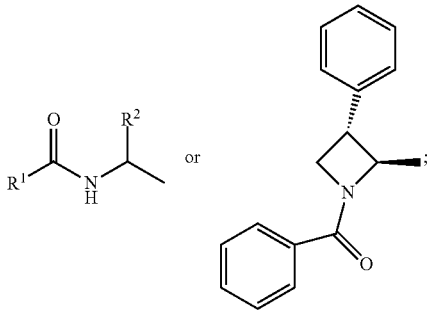

provided that $R^1$ is not $CH(NH_2)CH_2OH$ when each of $R^2$ is phenylalanine side chain, $R^3$ is arginine side chain and $R^{4'}$ is asparagine side chain;

(ii) trimeric NPS peptidomimetic IIA-IIE (IIA)

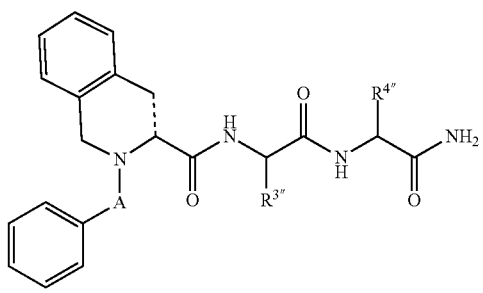

(IIB)

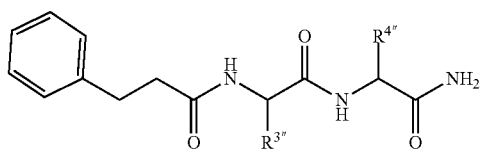

(IIC)

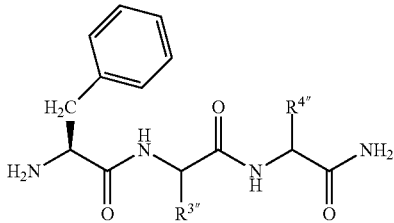

(IID)

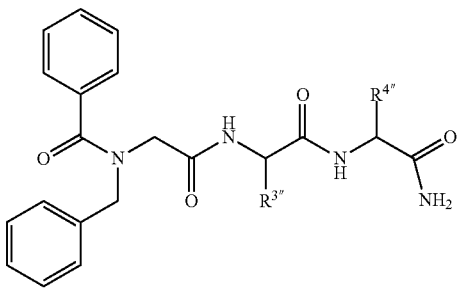

(IIE)

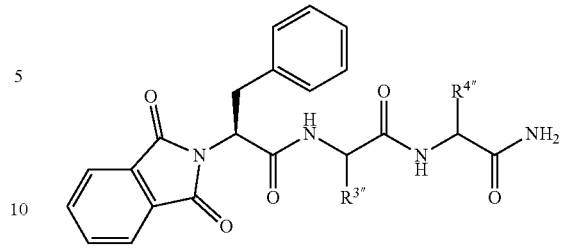

wherein $R^{3''}$ is arginine side chain, lysine side chain or $C_1$-$C_3$ alkyl;
$R^{4''}$ is asparagine side chain;
----- is a cis or trans bond; and
A is $CH_2$ or CO;

(iii) pentameric peptidomimetic (III)

(III)

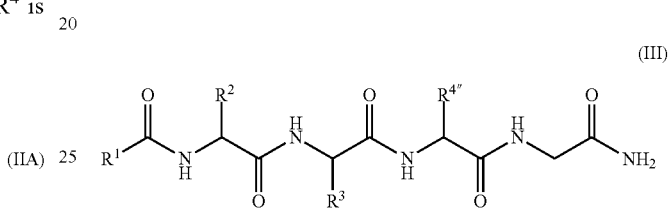

wherein $R^1$ is $CH(NHCH_3)CH_2OH$, $CH(NH_2)(CH_2)_2CH_3$, $CH(NH_2)CH_2OCH_3$, $CH_2CH_2OH$, $NHCH_2CH_3$, $CH(NH_2)CH_2OH$, $CH_2CH_2OCH_3$, branched or unbranched $C_1$-$C_6$ alkyl, heterocycle, heteroaryl, $C_1$-$C_4$ aralkyl, cycloalkyl, or aryl optionally substituted with halo, alkoxy, amino or alkoxyaminoalkyl;
$R^2$ is H, phenylalanine side chain, alkylcycloalkyl, unbranched $C_1$-$C_6$ alkyl, or benzyl optionally substituted with nitro or halo;
$R^3$ is arginine side chain or lysine side chain;
$R^{4''}$ is asparagine side chain;
provided that $R^1$ is not $CH(NH_2)CH_2OH$ when each of $R^2$ is phenylalanine side chain, $R^3$ is arginine side chain and $R^{4''}$ is asparagine side chain;

(iv) hexameric peptidomimetic (IV)

(IV)

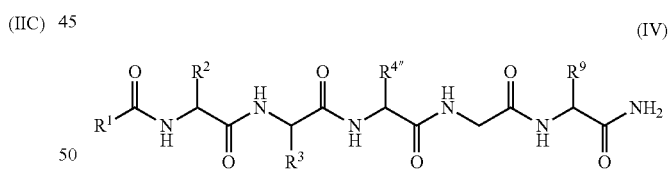

wherein $R^1$ is $CH(NHCH_3)CH_2OH$, $CH(NH_2)(CH_2)_2CH_3$, $CH(NH_2)CH_2OCH_3$, $CH_2CH_2OH$, $NHCH_2CH_3$, $CH(NH_2)CH_2OH$, $CH_2CH_2OCH_3$, branched or unbranched $C_1$-$C_6$ alkyl, heterocycle, heteroaryl, $C_1$-$C_4$ aralkyl, cycloalkyl, or aryl optionally substituted with halo, alkoxy, amino or alkoxyaminoalkyl;
$R^2$ is H, phenylalanine side chain, alkylcycloalkyl, unbranched $C_1$-$C_6$ alkyl, or benzyl optionally substituted with nitro or halo;
$R^3$ is arginine side chain or lysine side chain;
$R^{4''}$ is asparagine side chain; and
$R^9$ is a valine side chain or a phenylalanine side chain;
provided that $R^1$ is not $CH(NH_2)CH_2OH$ when each of $R^2$ is phenylalanine side chain, $R^3$ is arginine side chain and $R^{4''}$ is asparagine side chain; or a pharmaceutically acceptable salt thereof.

In another aspect, the disclosure relates to a pharmaceutical composition comprising the compounds of Formulas IA, IB, IC, ID, IIA, IIB, IIC, IID, IIE, III or IV and a pharmaceutically acceptable carrier.

In a further aspect, the disclosure relates to a method for treating a subject having a condition or disorder where modulation of neuropeptide S receptor activity is of therapeutic benefit, comprising administering to said subject having or susceptible to said condition or disorder a therapeutically effective amount of a compound according to Formula IA, IB, IC, ID IIA, IIB, IIC, IID, IIE, III or IV.

Other aspects, features and embodiments of the disclosure will be more fully apparent from the ensuing description and appended claims.

DETAILED DESCRIPTION OF THE DISCLOSURE, AND PREFERRED EMBODIMENTS THEREOF

Figure 1:
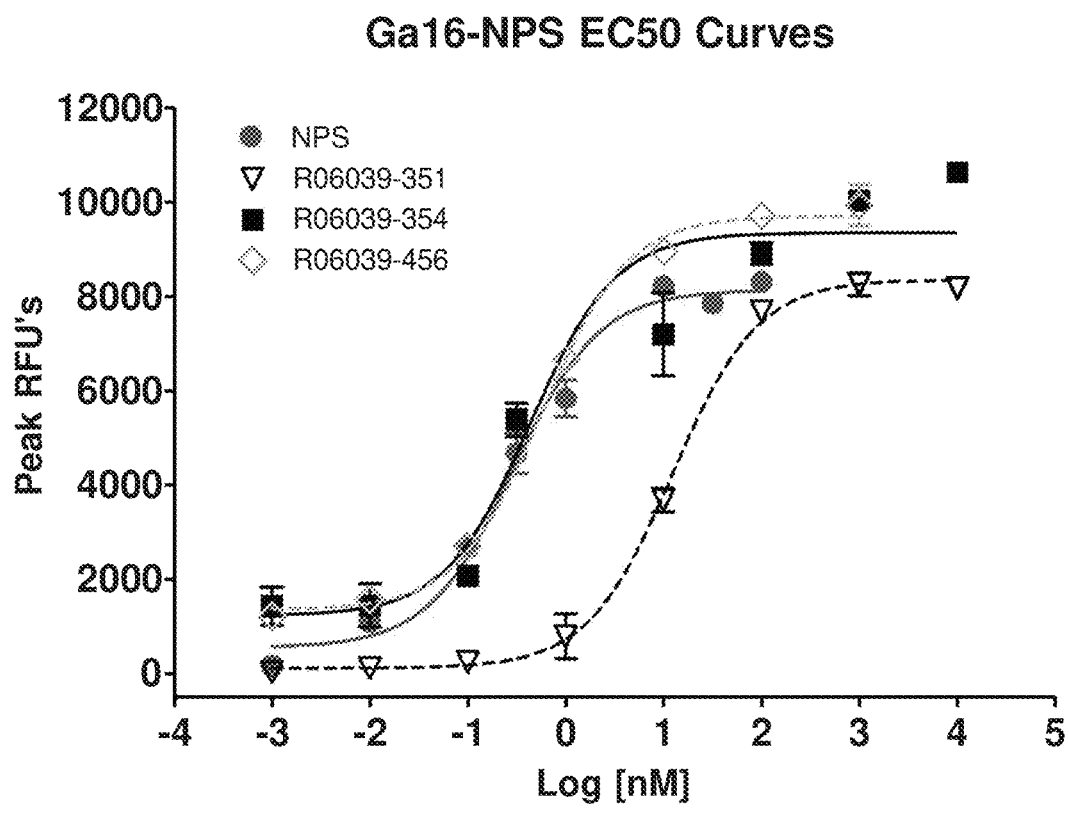
FIG. 1 is a graphical representation of dose response EC50 curves for compounds according to the present disclosure.

The present disclosure relates to neuropeptide S receptor agonists. The agonists of the disclosure include tripeptide, tetrapeptide, pentapeptide or hexapeptide analogs exhibiting affinity for and activity at the neuropeptide S receptor. The peptidomimeticmolecules according to the disclosure may thus be useful in the treatment of disorders, syndromes and conditions mediated by modulation of the neuropeptide S receptor.

Human neuropeptide S (hNPS) is a 20 residue peptide with the primary sequence SFRNGVGTGMKKTSFQRAKS (SEQ ID NO: 1). Studies of the structure-function relationships in the neuropeptide S receptor have shown that the $NH_2$ terminal third of NPS, in particular residues Phe-2, Arg-3, Asn-4 and Val-6 are necessary and sufficient for activation of NPSR. Bernier et al., *J. Biol. Chem.*, 281(34):24704-24712 (2006). According to this study, removal of the C-terminal 14 residues (peptide 1-6) has limited effect on the potency of the peptide, whereas removing Ser-1 (peptide 2-20) is detrimental to function and removing the first two (peptide 3-20) or three (peptide 4-20) $NH_2$-terminal residues results in largely inactive peptides. The study further stated that the results indicated that the first six residues, in particular residues Phe-2, Arg-3, Asn-4, and Val-6, are necessary for receptor activation, whereas residue Gly-7 is critically located and can modulate the inherent activity of the peptide.

According to another study, the effect of hNPS was mimicked by the fragment hNPS-(1-10), Phe-2, Arg-3 and Asn-4 are crucial for biological activity and the sequence Thr8-Gly9-Met10 is important for receptor activation. Roth et al., *J. Biol. Chem.*, 281(30):20809-20816 (2006). This study concluded that the sequence 1-10 was the smallest fragment able to activate the hNPSR with similar potencies and efficacies as full-length hNPS.

In view of these studies, other researchers have investigated the effects of making changes to various amino acids in the longer peptide hNPS, including structure activity studies at positions 3 and 4 of human neuropeptide S (Camarda et al., *Biog. & Med. Chem.* 16:8841-8845 (2008)), position 2 (Camarda et al., *J. Med Chem.* 51:655-658 (2008)) and position 5 (Guerrini et al., *J. Med. Chem.* 52:524-529, 4068-4071 (2009)).

The use of peptides as drugs may be limited by the following factors such as low metabolic stability towards proteolysis in the gastrointestinal tract and in serum, poor transport from the gastrointestinal tract to the blood and poor penetration into the central nervous system, among other issues. In view of the problems with using the full neuropeptideS ligand as a drug, the present disclosure provides small molecule peptidomimetic compounds which offer activity at the neuropeptide S receptor. It has unexpectedly been found that peptidomimetic trimers, tetramers, pentamers and hexamers of NPS have effective potency and selectivity for the NPS receptor, despite earlier studies which indicated that such truncated peptide structures would not be able to activate the hNPSR.

According to one aspect of the disclosure, tetrameric NPS peptidomimetic compounds IA-ID are provided:

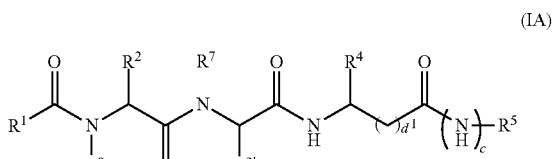

(IA)

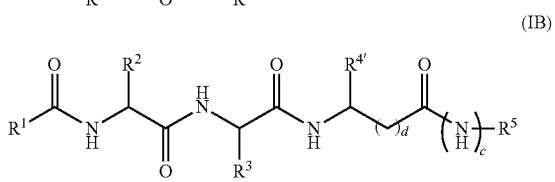

(IB)

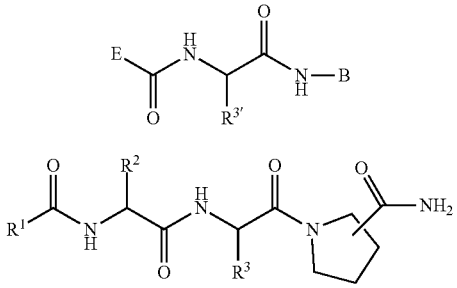

(IC)

(ID)

wherein R¹ is CH(NHCH₃)CH₂OH, CH(NH₂)(CH₂)₂CH₃, CH(NH₂)CH₂OCH₃, CH₂CH₂OH, NHCH₂CH₃, CH(NH₂)CH₂OH, CH₂CH₂OCH₃, branched or unbranched $C_1$-$C_6$ alkyl, heterocycle, heteroaryl, $C_1$-$C_4$ aralkyl, cycloalkyl, or aryl optionally substituted with halo, alkoxy, amino or alkoxyaminoalkyl;

R² is H, phenylalanine side chain, alkylcycloalkyl, unbranched $C_1$-$C_6$ alkyl, or benzyl substituted with nitro or halo;

R³ is arginine side chain or lysine side chain;

R³' is H, lysine side chain, $C_1$-$C_3$ alkylated or benzylated lysine side chain, alanine side chain, unbranched $C_1$-$C_6$ alkyl, (CH₂)₄NHCOCF₃, or benzyl optionally substituted with nitro;

R⁴ is asparagine side chain or $C_1$-$C_3$ alkyl;

R⁴' is H, asparagine side chain, $C_1$-$C_3$ alkyl heteroaryl, $C_1$-$C_6$ alkyl, CH₂OH, CH₂CONHCH₃, CH₂COOCH₃, CH₂CN;

R⁵ is H, OH, unbranched $C_1$-$C_6$ alkyl or $C_1$-$C_4$ alkylcycloalkyl;

c is 0 when R⁵ is OH, or c is 1 when R⁵ is hydrogen, unbranched $C_1$-$C_6$ alkyl or $C_1$-$C_4$ alkylcycloalkyl;

R⁷ is H or a lysine side chain, provided that when R⁷ is a lysine side chain, R³' is H;

R⁸ is H or CH₃;

d is 0 or, when R⁴' is H, d is 1, or when R⁴' is CH₃, d may be 0 or 1;

d¹ is 0 or, when R⁴ is CH₃, d¹ is 1;

B is a five membered saturated ring substituted with one C(O)NH₂ group or a six membered saturated or aromatic ring substituted with one C(O)NH₂ group; and E is

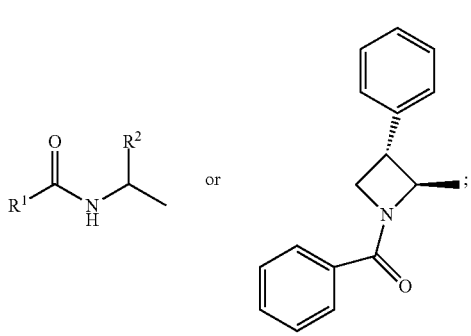

provided that R¹ is not CH(NH₂)CH₂OH when each of R² is phenylalanine side chain, R³ is arginine side chain and R⁴' is asparagine side chain, or a pharmaceutically acceptable salt thereof.

In an embodiment of Formula IA, R¹ is CH(NH₂)CH₂OH, R² is a phenylalanine side chain, R³' is an alkylated lysine side chain and R⁴ is an asparagine side chain.

In a further embodiment of Formula IA, R¹ is CH(NH₂)CH₂OH, R² is a alkylcycloalkyl, R³' is an alkylated lysine side chain and R⁴ is an asparagine side chain.

In a further embodiment of Formula IA, R¹ is an alkyl group, R² is a phenylalanine side chain, R³' is a lysine side chain and R⁴ is an asparagine side chain.

In a further embodiment of Formula IA, R¹ is phenyl, R² is a phenylalanine side chain, R³' is a lysine side chain and R⁴ is an asparagine side chain.

In a further embodiment of Formula IA, R¹ is phenyl, R² is a benzyl substituted with halo, R³' is a lysine side chain and R⁴ is an asparagine side chain.

In a further embodiment of Formula IA, R¹ is phenyl, R² is a phenylalanine side chain, R³' is an alkylated lysine side chain and R⁴ is an asparagine side chain.

In a further embodiment of Formula IA, R¹ is phenyl, R² is a phenylalanine side chain, R³' is a lysine side chain, R⁴ is an asparagine side chain and R⁵ is an unbranched alkyl group.

In an embodiment of Formula IC, the compound may be represented as:

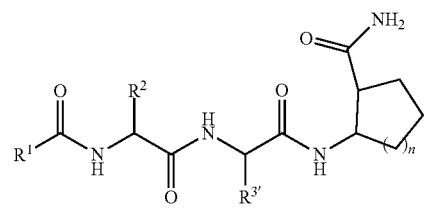

wherein R¹, R², and R³' are defined as above and n is 1 or 2.

In another embodiment according to Formula IC, the compound may be represented by the following:

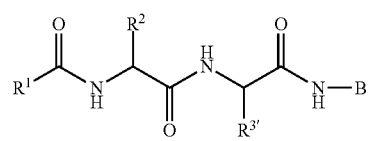

wherein R¹, R², and R³' are defined as above.

In another aspect of the disclosure, trimeric NPS peptidomimetic compounds IIA-IIE are provided:

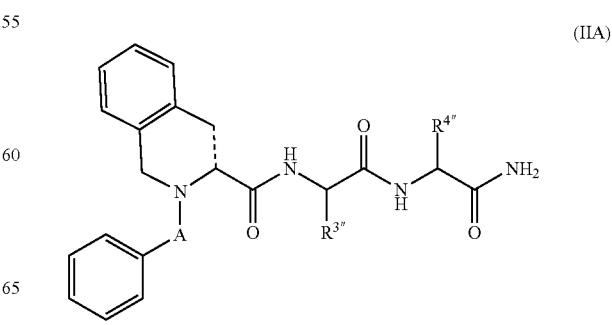

(IIA)

-continued

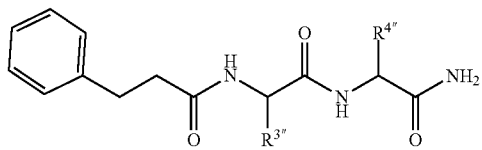

(IIB)

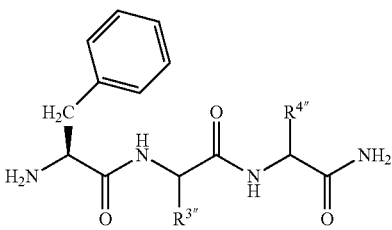

(IIC)

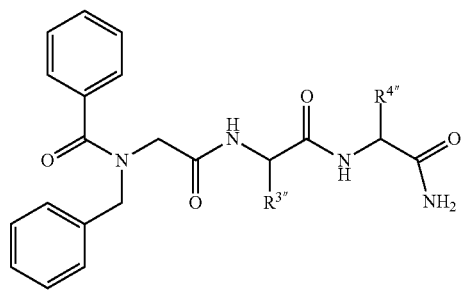

(IID)

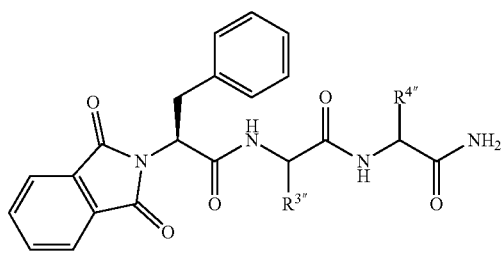

(IIE)

wherein R$^{3'}$ is arginine side chain, lysine side chain or C$_1$-C$_3$ alkyl;
R$^{4''}$ is asparagine side chain;
----- is a cis or trans bond; and
A is CH$_2$ or CO, or a pharmaceutically acceptable salt thereof.

In a further aspect of the disclosure pentameric NPS peptidomimetic compounds according the Formula III are provided:

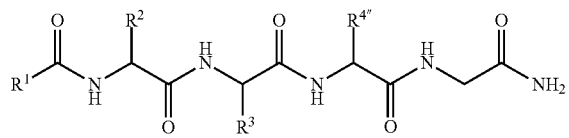

(III)

wherein R$^1$ is CH(NHCH$_3$)CH$_2$OH, CH(NH$_2$)(CH$_2$)$_2$CH$_3$, CH(NH$_2$)CH$_2$OCH$_3$, CH$_2$CH$_2$OH, NHCH$_2$CH$_3$, CH(NH$_2$) CH$_2$OH, CH$_2$CH$_2$OCH$_3$, branched or unbranched C$_1$-C$_6$ alkyl, heterocycle, heteroaryl, C$_1$-C$_4$ aralkyl, cycloalkyl, or aryl optionally substituted with halo, alkoxy, amino or alkoxyaminoalkyl;
R$^2$ is H, phenylalanine side chain, alkylcycloalkyl, unbranched C$_1$-C$_6$ alkyl, or benzyl optionally substituted with nitro or halo;
R$^3$ is arginine side chain or lysine side chain;
R$^{4''}$ is asparagine side chain;
provided that R$^1$ is not CH(NH$_2$)CH$_2$OH when each of R$^2$ is phenylalanine side chain, R$^3$ is arginine side chain and R$^{4''}$ is asparagine side chain, or a pharmaceutically acceptable salt thereof.

In a still further aspect of the disclosure, hexameric NPS peptidomimetics according to Formula IV are provided:

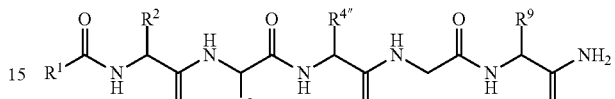

(IV)

wherein R$^1$ is CH(NHCH$_3$)CH$_2$OH, CH(NH$_2$)(CH$_2$)$_2$CH$_3$, CH(NH$_2$)CH$_2$OCH$_3$, CH$_2$CH$_2$OH, NHCH$_2$CH$_3$, CH(NH$_2$) CH$_2$OH, CH$_2$CH$_2$OCH$_3$, branched or unbranched C$_1$-C$_6$ alkyl, heterocycle, heteroaryl, C$_1$-C$_4$ aralkyl, cycloalkyl, or aryl optionally substituted with halo, alkoxy, amino or alkoxyaminoalkyl;
R$^2$ is H, phenylalanine side chain, alkylcycloalkyl, unbranched C$_1$-C$_6$ alkyl, or benzyl optionally substituted with nitro or halo;
R$^3$ is arginine side chain or lysine side chain;
R$^{4''}$ is asparagine side chain; and
R$^9$ is a valine side chain or a phenylalanine side chain;
provided that R$^1$ is not CH(NH$_2$)CH$_2$OH when each of R$^2$ is phenylalanine side chain, R$^3$ is arginine side chain and R$^{4''}$ is asparagine side chain, or a pharmaceutically acceptable salt thereof.

Terms are used within their accepted meanings. The following definitions are meant to clarify, but not limit, the terms defined.

As used herein, the singular forms "a", "and", and "the" include plural referents unless the context clearly dictates otherwise.

A peptidomimetic refers to a compound that bears identifiable resemblance to a peptide, or portion of a peptide, that, as the ligand of a biological receptor, can mimic or block the biological effects of a natural peptide. A peptide analog is a peptidomimetic where one or more sidechains or other portions of the peptide molecule have been modified.

As used herein, the identification of a carbon number range, e.g., in C$_1$-C$_{12}$ alkyl, is intended to include each of the component carbon number moieties within such range, so that each intervening carbon number and any other stated or intervening carbon number value in that stated range, is encompassed, it being further understood that sub-ranges of carbon number within specified carbon number ranges may independently be included in smaller carbon number ranges, within the scope of the invention, and that ranges of carbon numbers specifically excluding a carbon number or numbers are included in the invention, and sub-ranges excluding either or both of carbon number limits of specified ranges are also included in the disclosure.

Accordingly, C$_1$-C$_{12}$ alkyl is intended to include methyl, ethyl, propyl, butyl, pentyl, hexyl, heptyl, octyl, nonyl, decyl, undecyl and dodecyl, including straight chain as well as branched groups of such types, such as isopropyl and tert-butyl. It therefore is to be appreciated that identification of a carbon number range, e.g., C$_1$-C$_{12}$ or C$_1$-C$_6$, as broadly applicable to a substituent moiety, enables, in specific embodiments of the disclosure, the carbon number range to be further restricted, as a sub-group of moieties having a carbon number range within the broader specification of the substituent moiety. By way of example, the carbon number range e.g., $C_1$-$C_{12}$ alkyl, may be more restrictively specified, in particular embodiments of the disclosure, to encompass sub-ranges such as $C_1$-$C_4$ alkyl, $C_2$-$C_8$ alkyl, $C_2$-$C_4$ alkyl, $C_3$-$C_5$ alkyl, or any other sub-range within the broad carbon number range. Thus, for example, the range $C_1$-$C_6$ would be inclusive of and can be further limited by specification of sub-ranges such as $C_1$-$C_3$, $C_1$-$C_4$, $C_2$-$C_6$, $C_4$-$C_6$, etc. within the scope of the broader range.

"Cycloalkyl" refers to an optionally substituted non-aromatic cyclic hydrocarbon ring. Unless otherwise indicated, cycloalkyl is composed of three to eight carbon atoms. Exemplary "cycloalkyl" groups include, but are not limited to, cyclopropyl, cyclobutyl, cyclopentyl, cyclohexyl, and cycloheptyl.

"Heterocycle" refers to saturated or unsaturated cyclic radicals containing one or more heteroatoms (e.g., O, N, S) as part of the ring structure and having two to seven carbon atoms in the ring. In embodiments, a heterocycle may be fused to an aryl group such as phenyl.

"Heteroaryl" refers to unsaturated aromatic cyclic radicals containing one or more heteroatoms (e.g., O, N, S) as part of the ring structure and having two to seven carbon atoms in the ring.

"Aryl" as used herein includes hydrocarbons derived from benzene or a benzene derivative that are unsaturated aromatic carbocyclic groups of from 6 to 10 carbon atoms. The aryls may have a single or multiple rings. One example is a phenyl group.

"Aralkyl" refers to aryl-substituted alkyl radicals. Aralkyl groups include benzyl and phenethyl.

"Alkylcycloalkyl" refers to cycloalkyl-substituted alkyl radicals.

The compounds of the disclosure may be further specified in specific embodiments by provisos or limitations excluding specific substituents, groups, moieties or structures, in relation to various specifications and exemplifications thereof set forth herein. Thus, the disclosure contemplates restrictively defined compositions, e.g., a composition wherein R is $C_1$-$C_{12}$ alkyl, with the proviso that R≠Ci alkyl when $R^1$ is a specified molecular component, and i is a specific carbon number.

When chiral centers are present the stereochemistry of the structures includes both R and S configuration, unless otherwise indicated.

The disclosure, as variously set out herein in respect of various described features, aspects and embodiments, may in particular implementations be constituted as comprising, consisting, or consisting essentially of, some or all of such features, aspects and embodiments, as well as elements and components thereof being aggregated to constitute various further implementations of the disclosure. The disclosure contemplates such features, aspects and embodiments in various permutations and combinations, as being within the scope of the disclosure. The disclosure may therefore be specified as comprising, consisting or consisting essentially of, any of such combinations and permutations of these specific features, aspects and embodiments, or a selected one or ones thereof.

The peptidomimetic compounds of the disclosure have full and partial agonist activity for the NPS receptor. EC50 values range from 1-4516 nM.

Embodiments of Formulas IA or IB may be represented by the following structures:

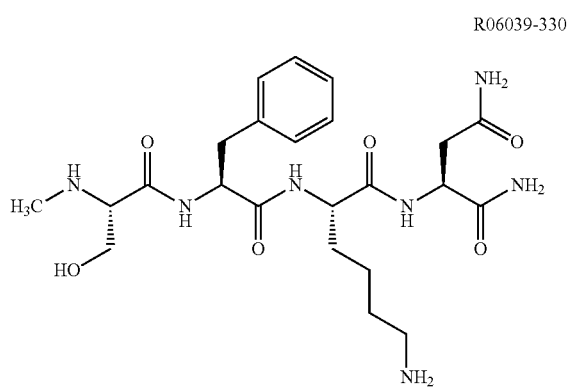

R06039-330

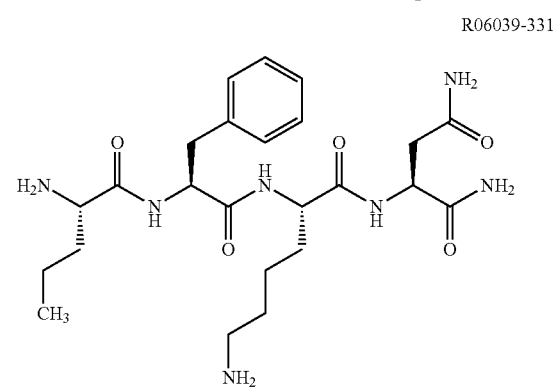

R06039-331

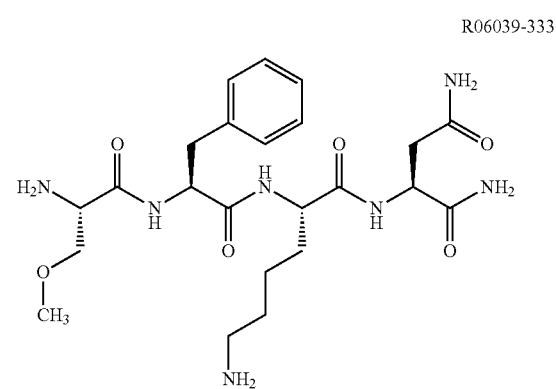

R06039-333

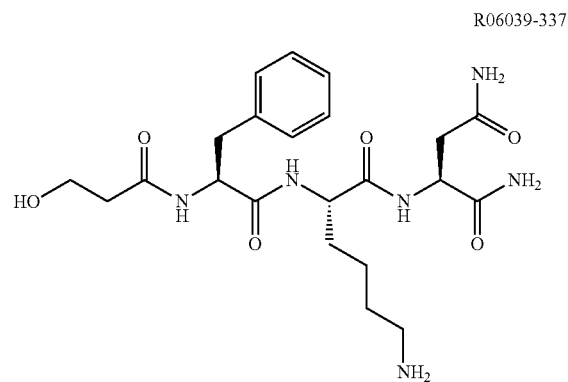

R06039-337

-continued
R06039-350
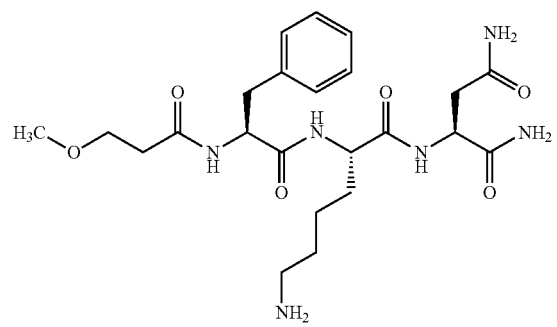
R06039-351
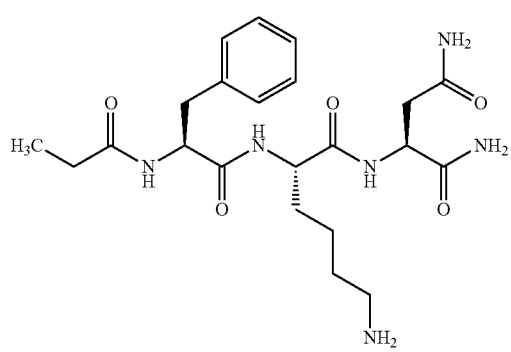
R06039-352
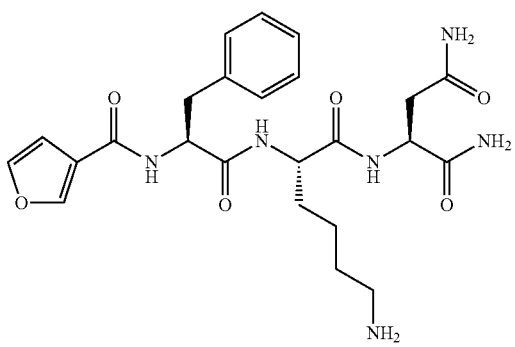
R06039-354
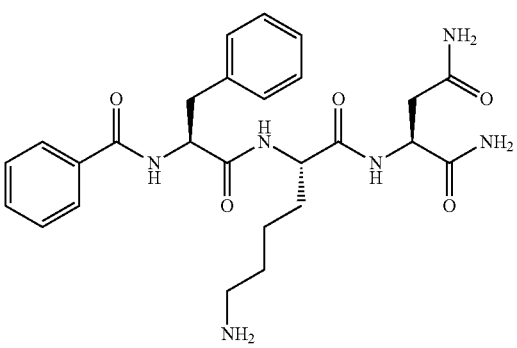
R06039-355
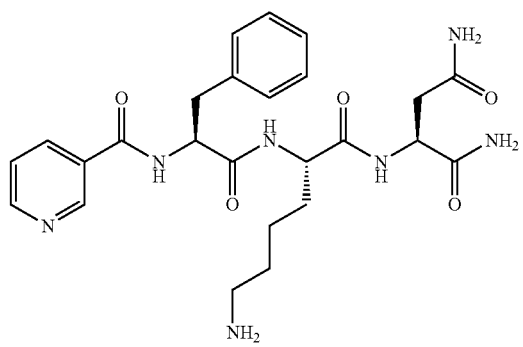
R06039-356
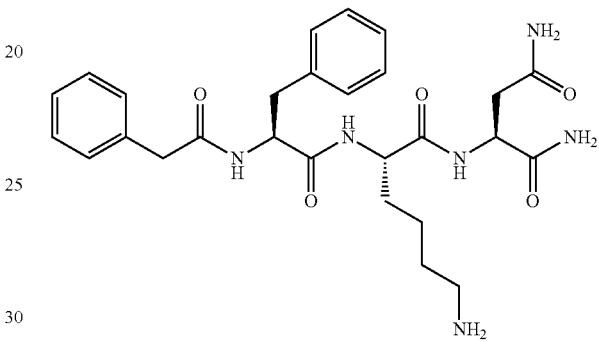
R06039-357
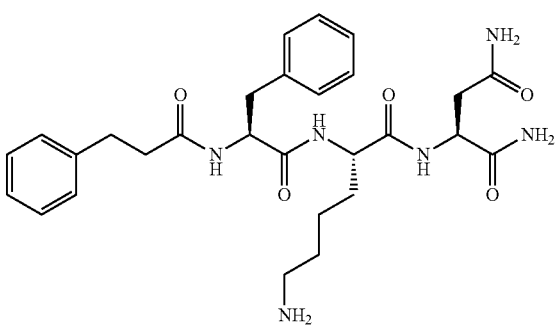
R06039-365
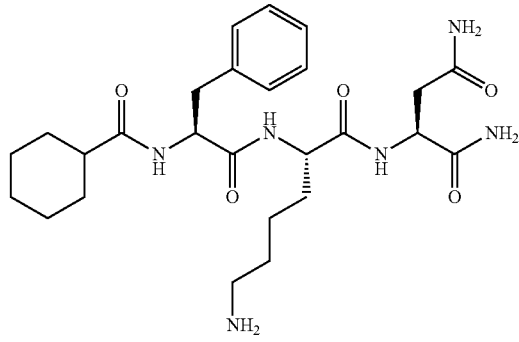

15
-continued

R06039-366

R06039-372

R06039-374

R06039-377

16
-continued

R06039-378

R06039-380

R06039-381

R06039-382

-continued
R06039-383
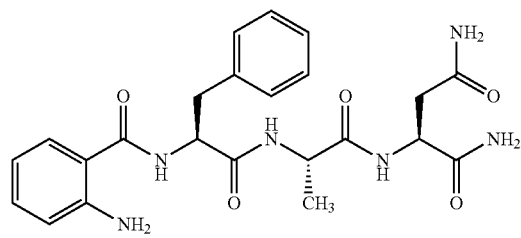
R06039-393
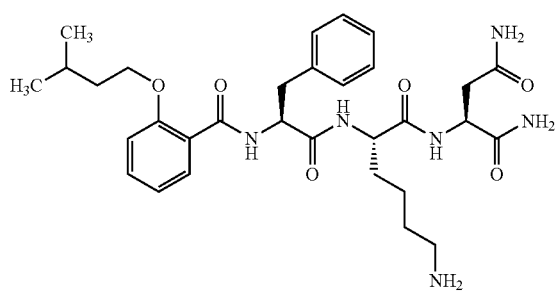
R06039-476
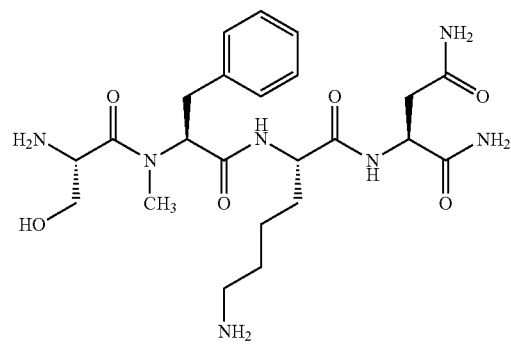
R06039-399
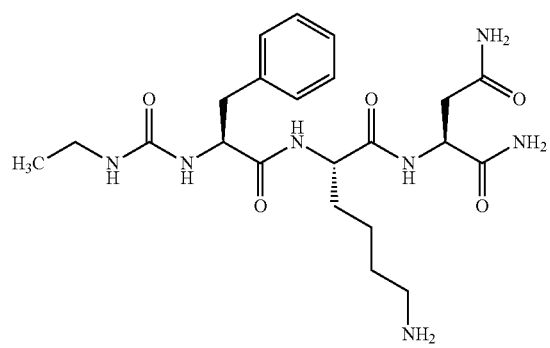
-continued
R06039-329
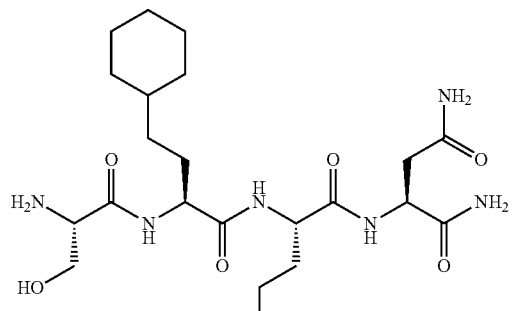
R06039-336
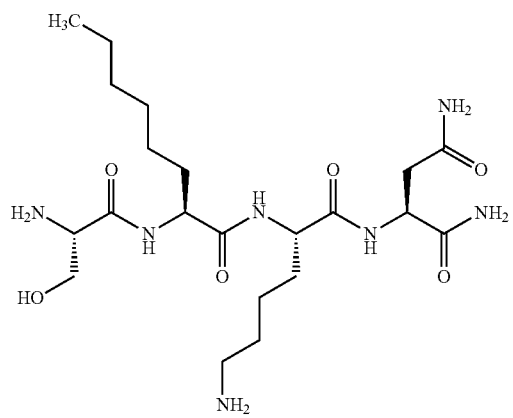
R06039-371
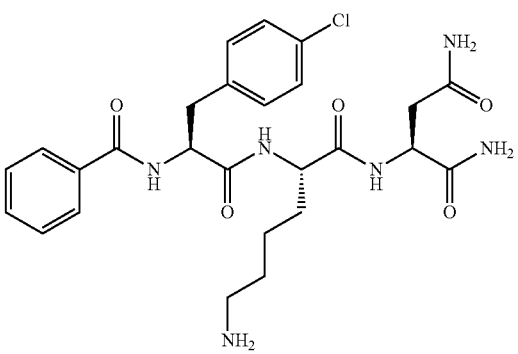
R06039-405
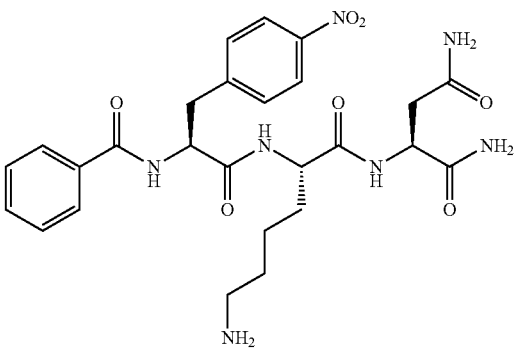

-continued
R06039-406
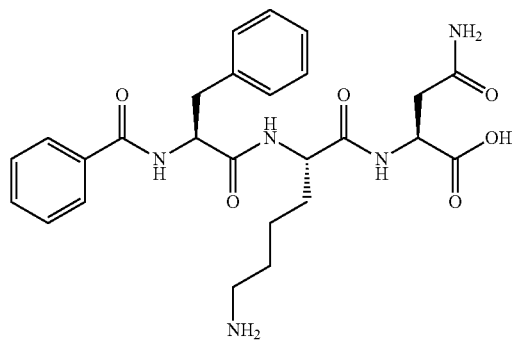
R06039-420
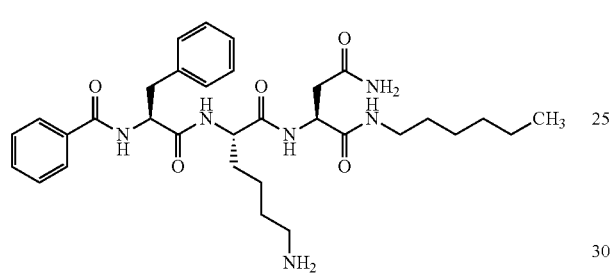
R06039-435
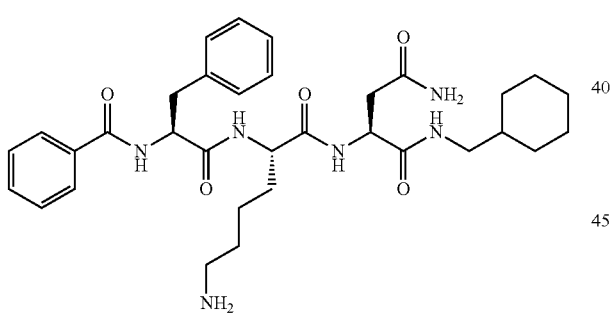
R06039-463
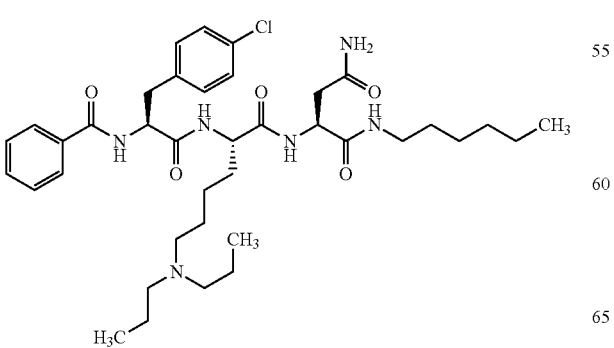
-continued
R06039-263
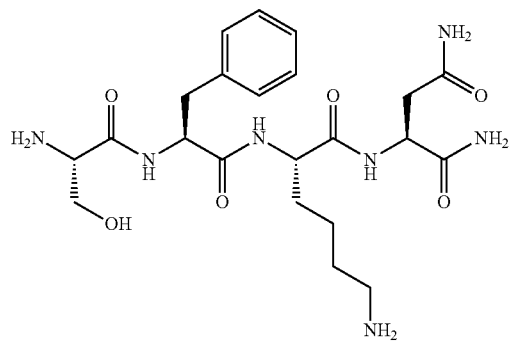
R06039-264
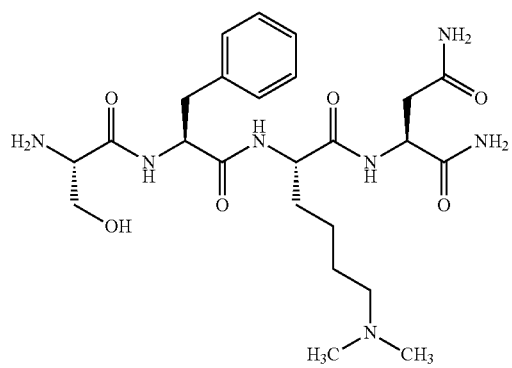
R06039-335
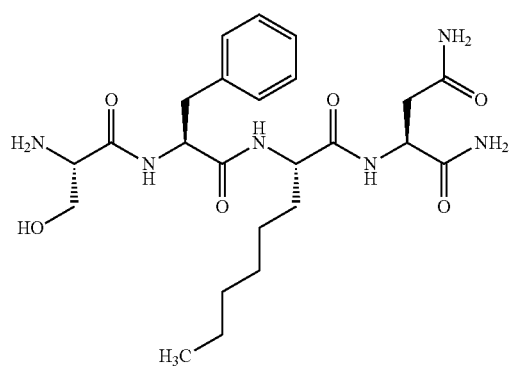
R06039-353
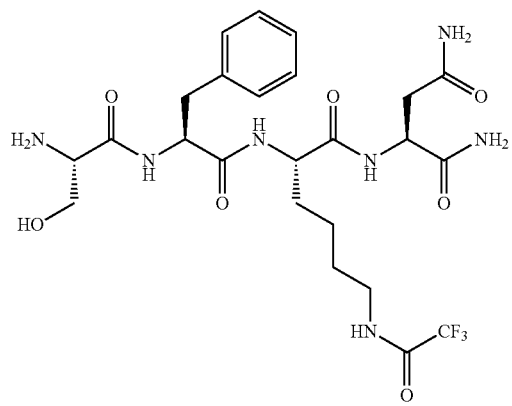

21
-continued
R06039-379
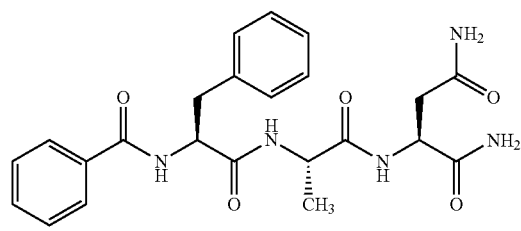
R06039-398
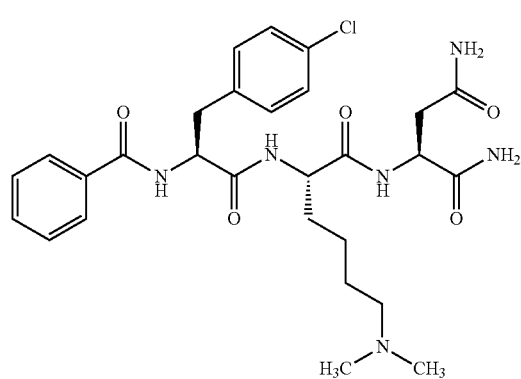
R06039-408
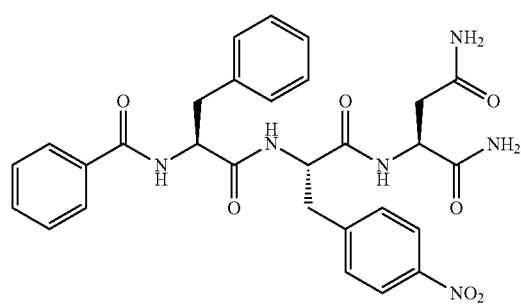
R06039-431
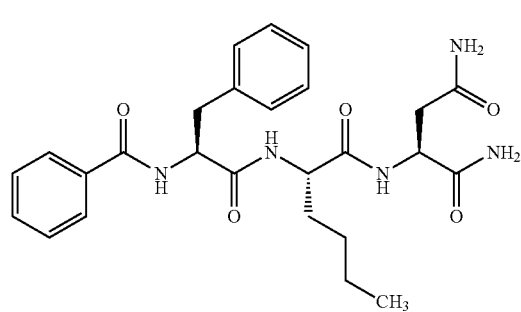
22
-continued
R06039-456
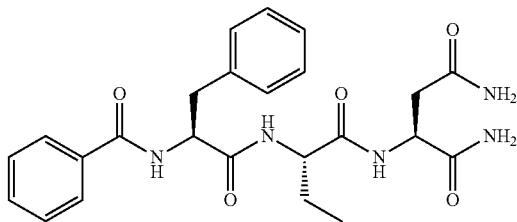
R06039-457
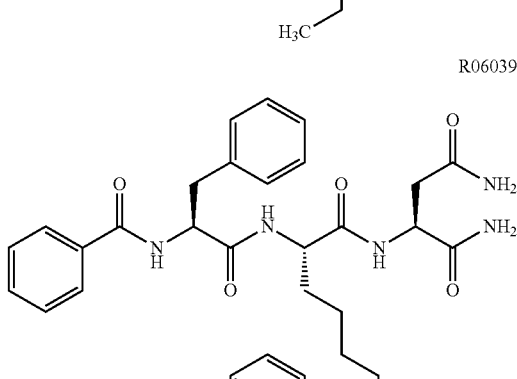
R06039-484
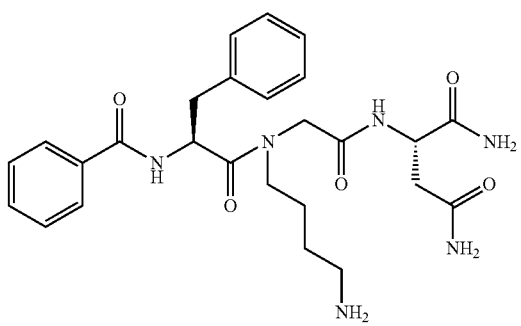
R06039-501
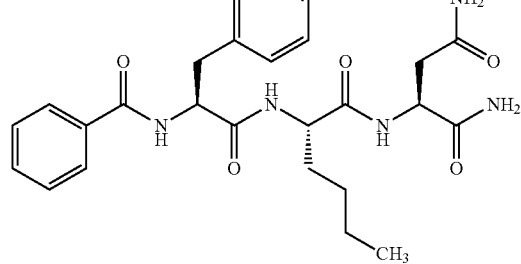

R06039-396
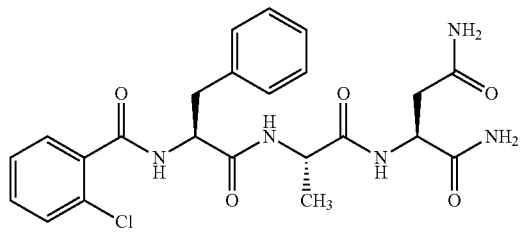
R06039-398
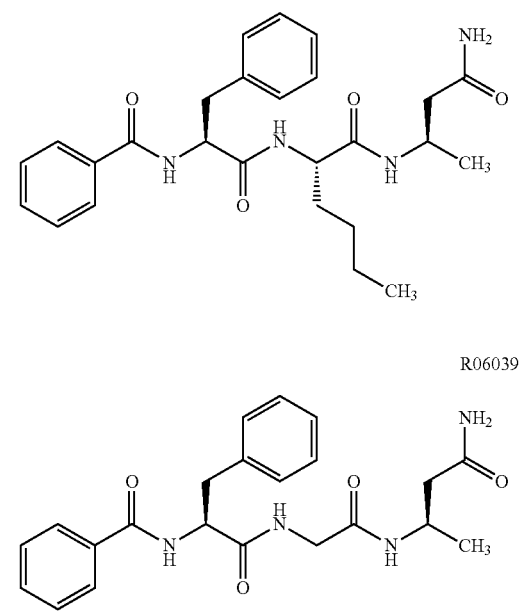
R06039-546
R06039-547
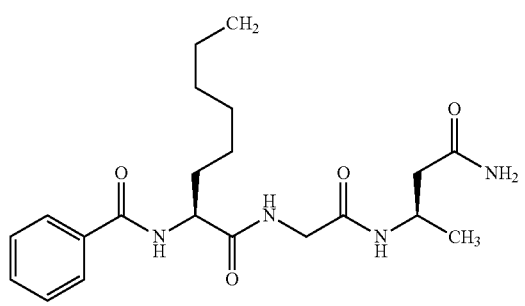
R06039-549
Embodiments of Formula IB may be represented b the following structures:
R06039-386
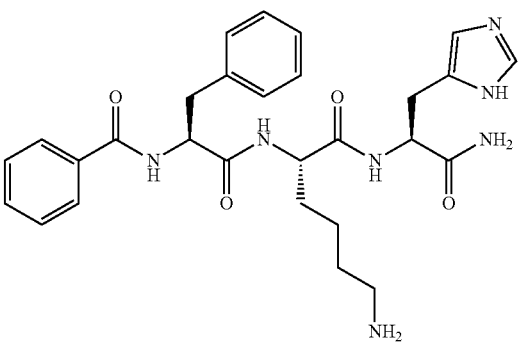
R06039-387
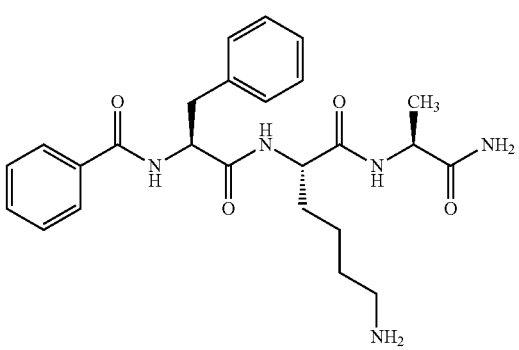
R06039-388
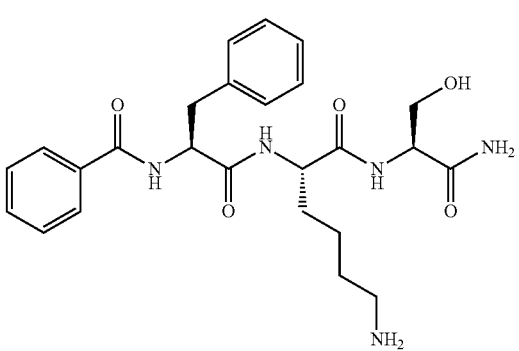
R06039-391
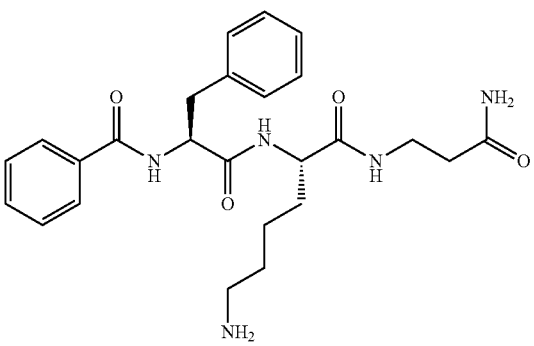

R06039-471
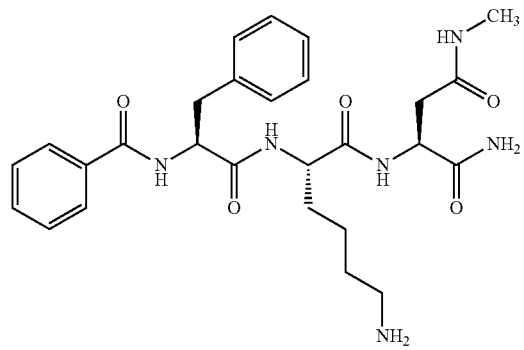
R06039-510
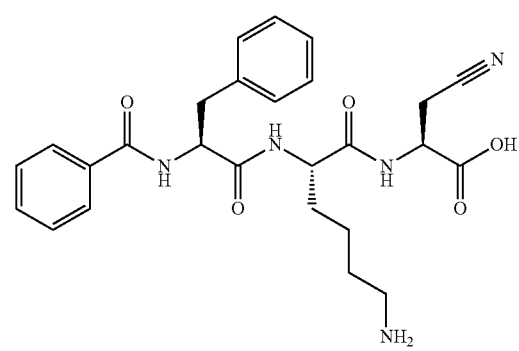
R06039-492
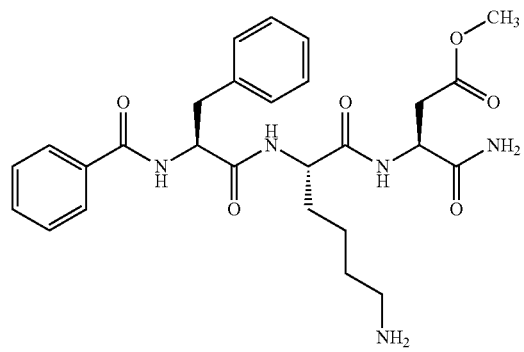
R06039-509
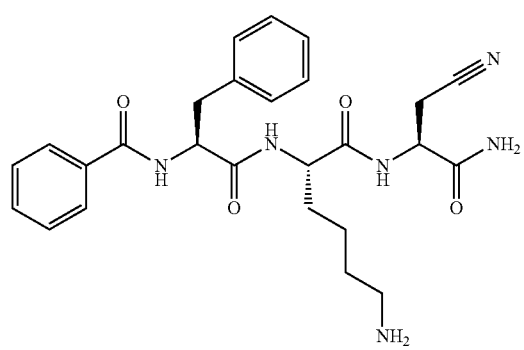
R06039-559
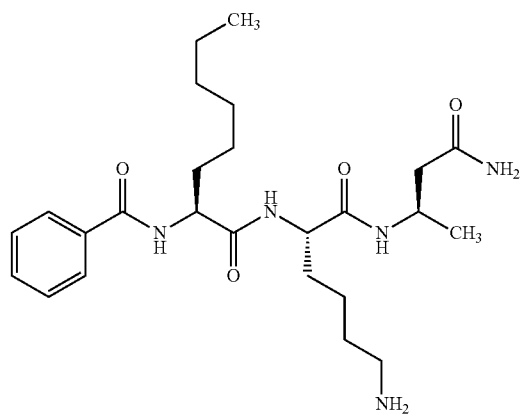
R06039-560
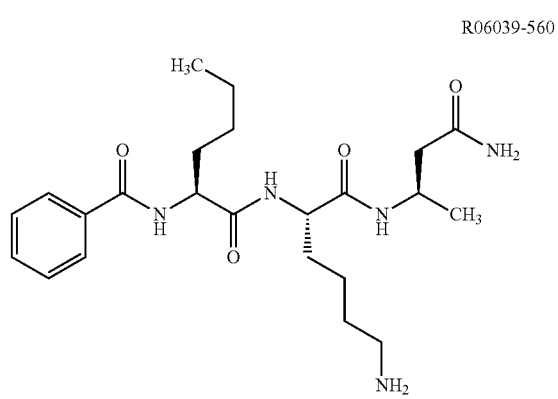
R06039-541
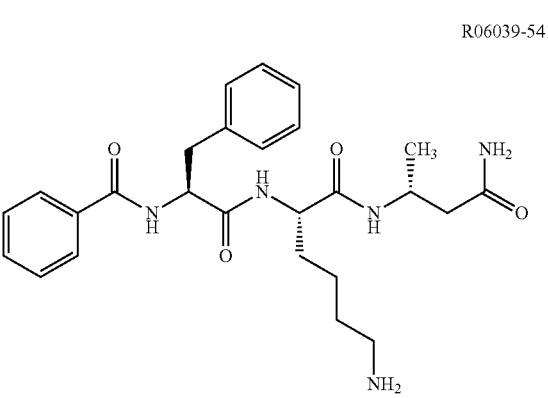
The following compounds are representative of compounds according to Formula IC:
R06039-551
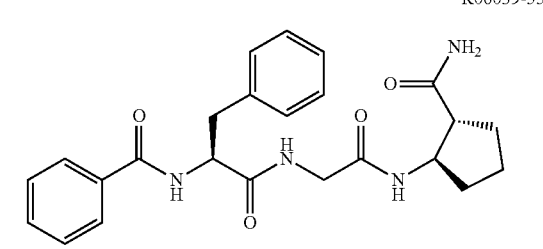

R06039-552
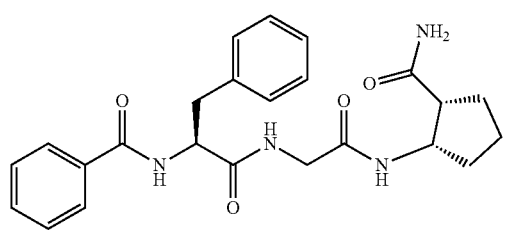
R06039-556
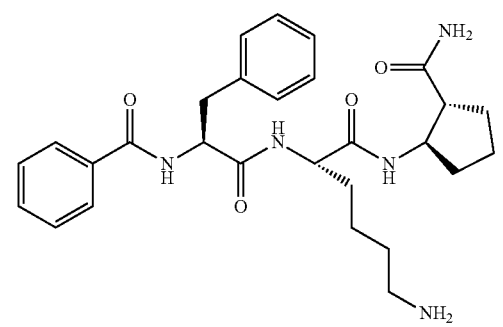
R06039-558
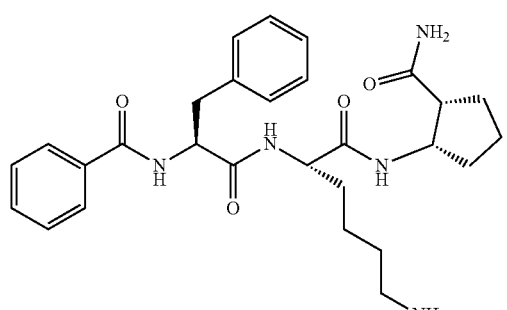
R06039-569
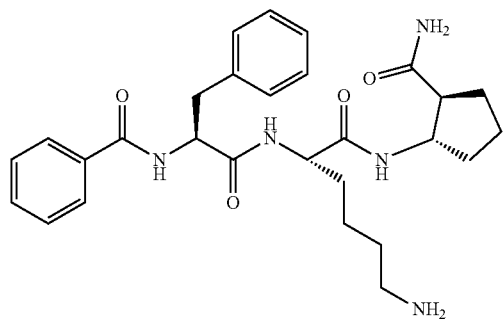
R06039-577
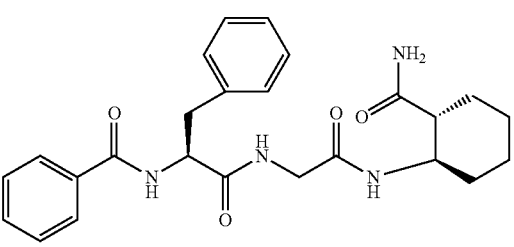
R06039-578
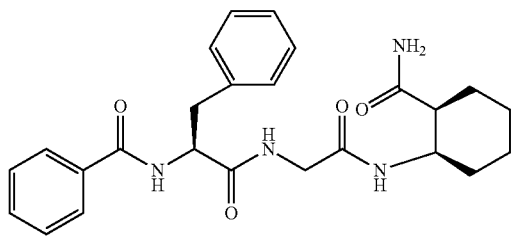
R06039-589
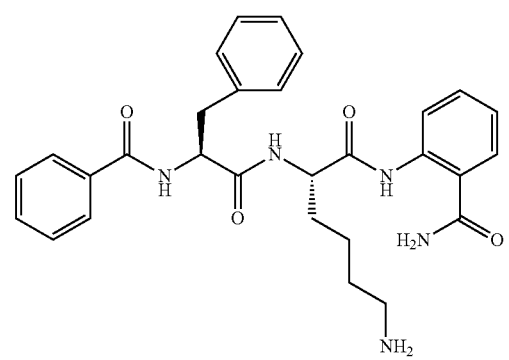
R06039-590
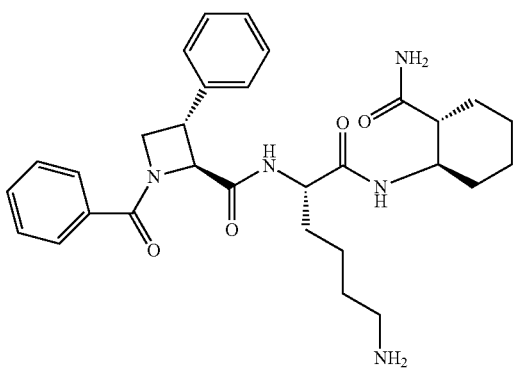
R06039-593
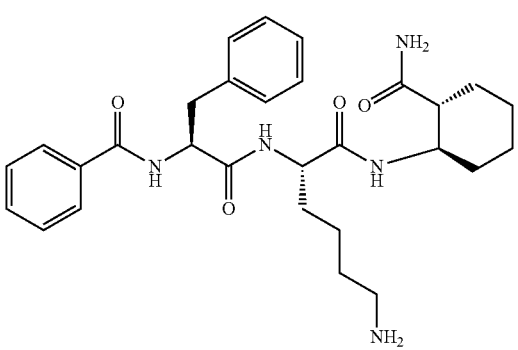

The following compounds are representative of compounds according to Formula ID:
The following compounds are representative of compounds according to Formula IIA:
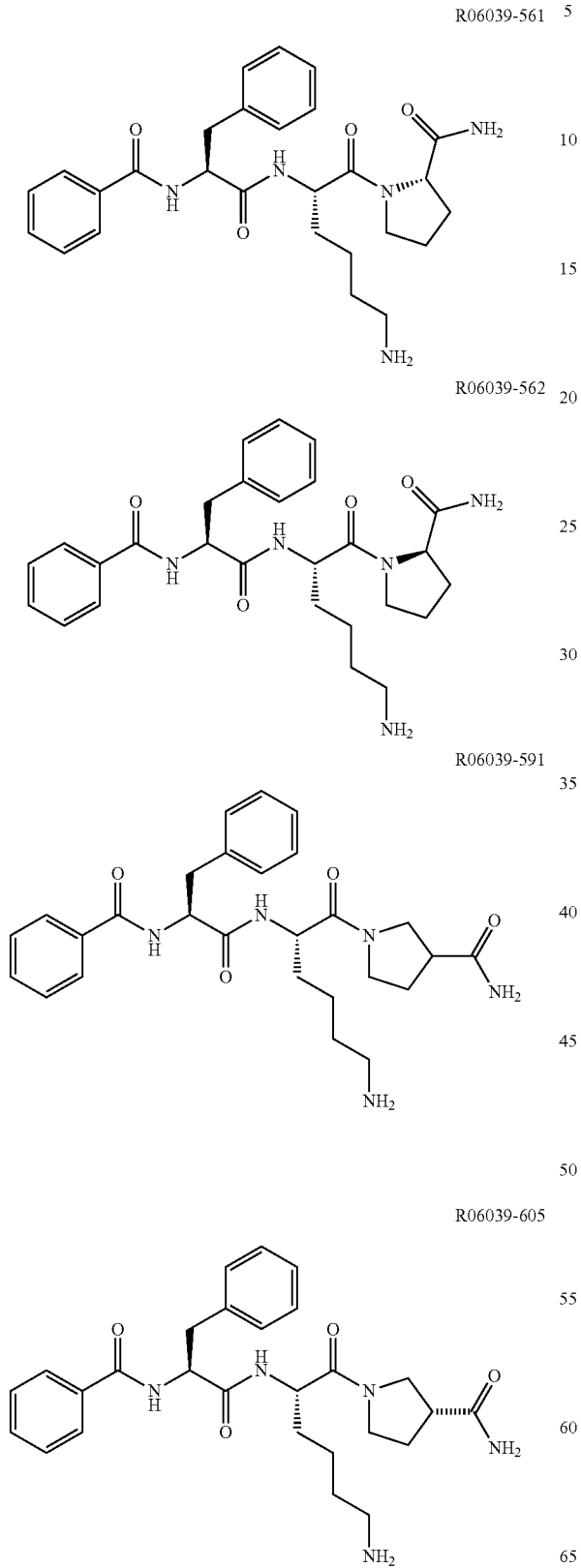
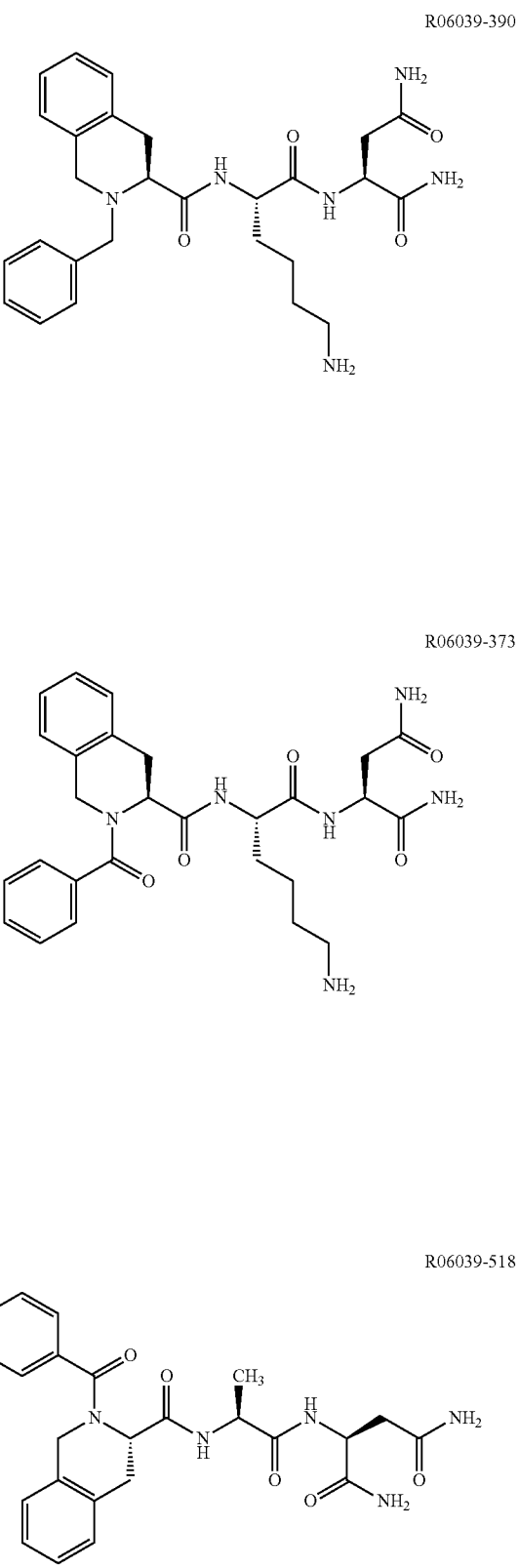

The following compound is representative of a compound according to Formula IIB:

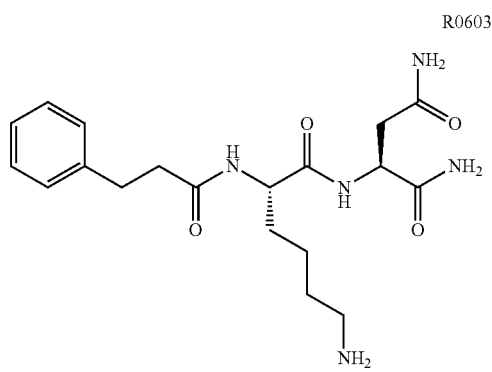

R06039-359

The following compound is representative of a compound according to Formula IIC:

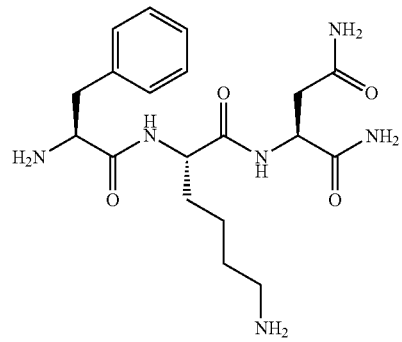

R06039-358

The following compound is a representative of a compound according to Formula IID:

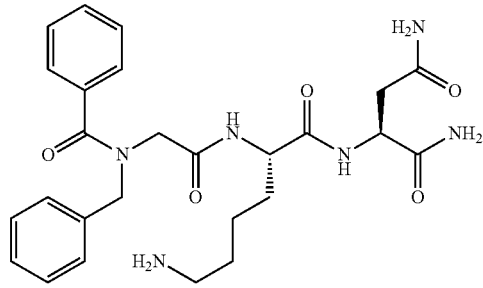

R06039-392

The following compound is representative of a compound of Formula IIE:

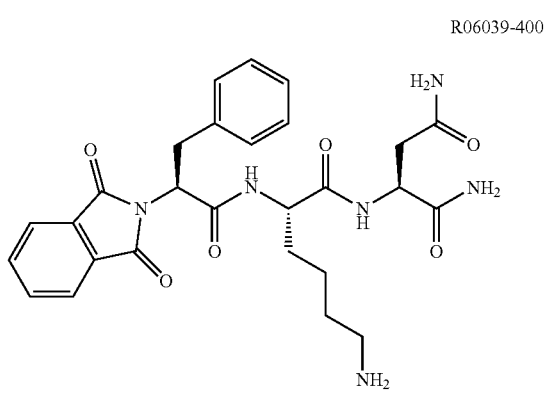 [SMILES: NCCCC[C@H](NC(=O)[C@H](Cc1ccccc1)N1C(=O)c2ccccc2C1=O)C(=O)N[C@@H](CC(N)=O)C(N)=O]

R06039-400

Embodiments of Formula IV may be represented by the following structures:

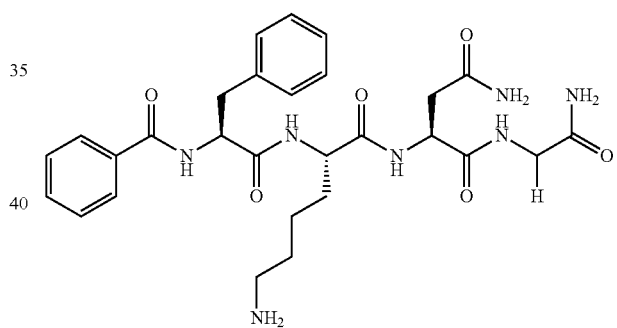

R06039-361

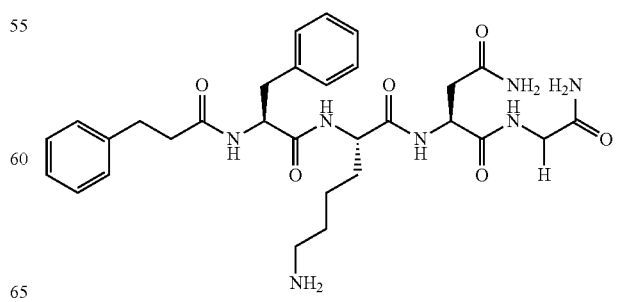

R06039-362

Embodiments of Formula V may be represented by the following structures:
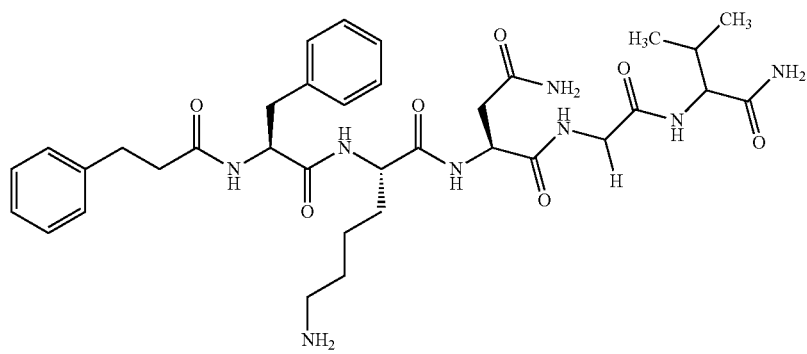
R06039-363
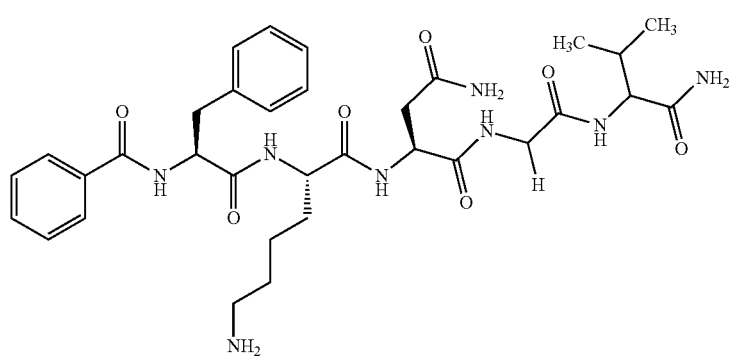
R06039-364
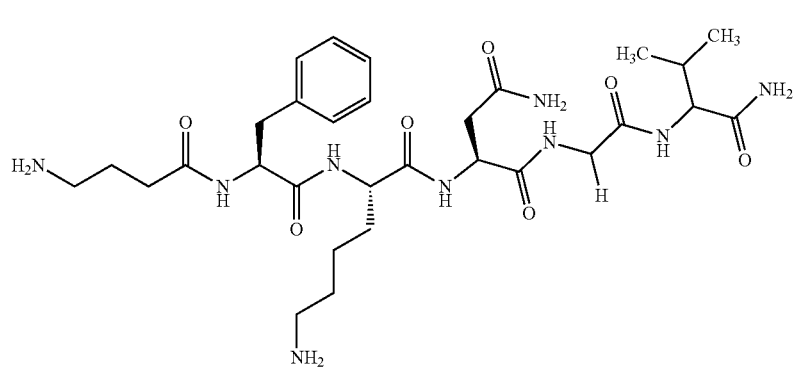
R06039-367
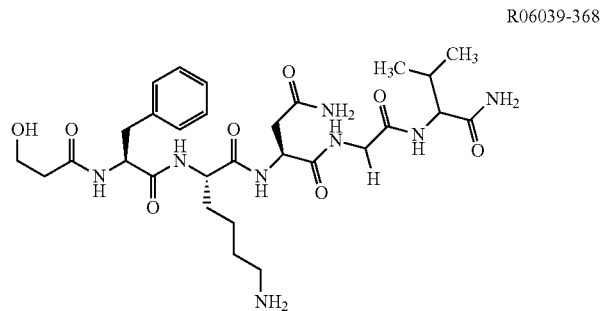
R06039-368
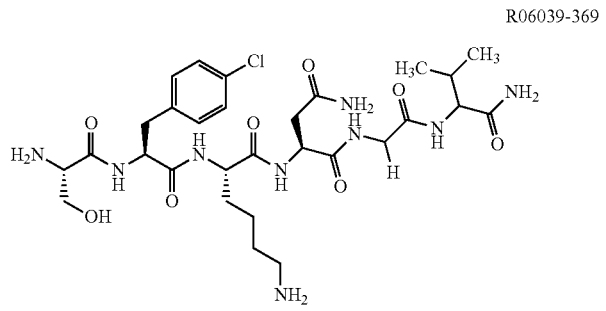
R06039-369

R06039-370

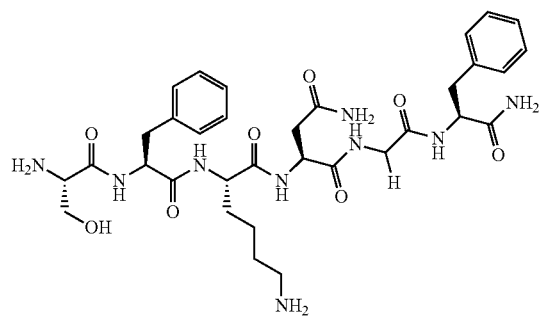

R06039-375

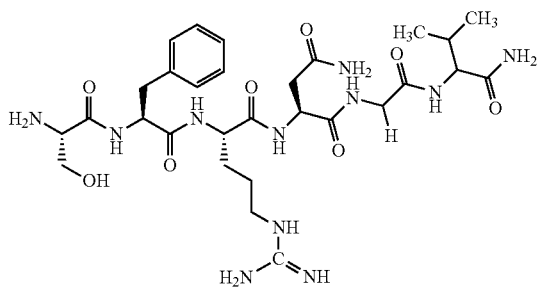

R06039-376

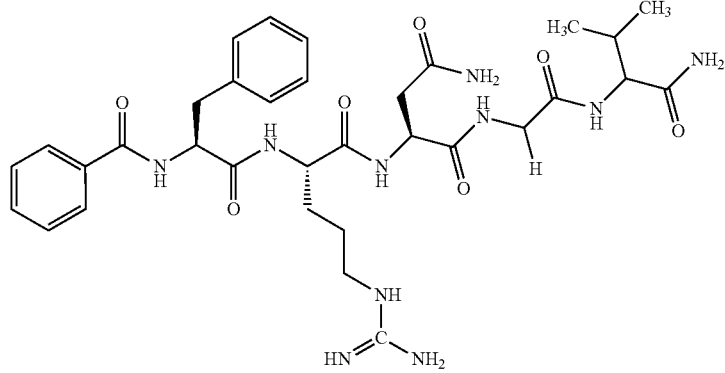

The neuropeptide S receptor has at least three known isoforms including the wild type NPS Asn[107], the NPS Asn107Ile and NPS C-Alt. Since each variant could potentially have functional difference, the agonist sensitivity of each isoform was evaluated. Radioligand binding of [$^{125}$I] Tyr[10]-NPS was unaltered among receptor variants; however, a 5-10 fold enhancement in functional sensitivity using calcium flux was observed for the Ile[107] variant over Asn[107]. In a functional assay, hNPS was the least potent at NPSR-C-Alt (30-fold lower versus the 107I variant).

In situ hybridization has shown that NPS receptor mRNA was expressed widely throughout the CNS. In particular, high levels of NPS receptor mRNA were identified in the thalamus, hypothalamus, cortex, hippocampus, and amygdala. Human NPS precursor mRNA, however, is largely expressed in the locus ceruleus (LC) of the brainstem and is cleaved from an 89 AA signal peptide at a specific cleavage site adjacent to the amino acids Arg Lys. Due to mRNA localization in the LC, NPS was hypothesized to play a role in arousal, anxiety, or both. The arousal and anxiolytic promoting properties of NPS has since been confirmed using stress-induced hypothermia. In view of these properties, the NPS receptor system may be useful as a target for non-sedating anxiolytics.

Other studies have found evidence for the role NPS plays in the sleep-wake cycle and a specific association between usual bedtime and the NPS N107I SNP was discovered. Thus, NPS pharmacotherapies may benefit patients suffering from insomnia or narcolepsy.

NPSR mRNA is expressed at very high levels in hippocampal areas known for regulating learning and memory such as the endopiriform cortex/nucleus and the subiculum. Therefore, NPS may be involved in memory and the consolidation of memory. NPS administration dose-dependently improved performance in novel recognitions assays, confirming a biochemical role in memory.

NPS is also implicated in the induction of acute anxiolytic-like effects in addition to the simultaneous reduction in the consolidation of aversive memories. NPS was found to be involved in mitigating fear expression as opposed to inhibiting fear learning. Thus, the activation of the NPS receptor has been found to possess a dual role in mitigating anxiety. In addition to the acute effects NPS has on anxiety, the more important role of facilitating extinction of aversive memories has been identified. The NPS agonist compounds and compositions of the disclosure may thus be useful to effectively treat anxiety and anxiety-related disorders such as post-traumatic stress disorder (PTSD).

In one aspect of the disclosure, methods of treating a variety of disorders and conditions modulated by the neuropeptide S receptor are provided. The NPS receptor agonists of the disclosure may be useful for substance abuse, narcolepsy, insomnia, obesity, cognitive decline, dementia, Alzheimer's disease, panic disorder, generalized anxiety, PTSD, phobias, schizophrenia and as supportive medication during any kind of cessation program in cognitive behavioral therapy, by way of example, such as drug addiction, eating disorders and gambling.

The term "effective amount" means that amount of a drug or pharmaceutical agent that will elicit the biological or medical response of a tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

In one aspect of the disclosure, the compounds and compositions of the disclosure may be used in combination with other drugs or agents, or in conjunction with a variety of psychotherapies useful in the treatment of the type of conditions and disorders modulated by the NPS receptor. Drugs or agents which may be used with the compounds and compositions of the disclosure may include typical and/or atypical antipsychotics such as haloperidol and aripiperazole or monoamine reuptake inhibitors such as fluoxetine and sertraline.

In another aspect of the disclosure, a method for treating a subject having a condition or disorder where modulation of neuropeptide S receptor activity is of therapeutic benefit is provided, the method comprising administering to said subject having or susceptible to said condition or disorder an effective amount of a compound demonstrating selective binding for a neuropeptide S receptor and exhibiting functional agonist activity for a neuropeptide S receptor.

In one aspect of the disclosure, a method is provided for treating a subject having a condition or disorder where modulation of neuropeptide S receptor activity is of therapeutic benefit comprising administering to said subject having or susceptible to said condition or disorder an effective amount of a tetrameric peptidomimetic analog compound according to any one of Formulas IA-ID, a trimeric peptidomimetic analog compound according to one of Formula IIA-IIE, a pentameric peptidomimetic analog compound according to Formula III, or a hexameric peptidomimetic analog according to Formula IV demonstrating selective binding and functional agonist activity at a neuropeptide S receptor. In embodiments, the compound administered is a pharmaceutically acceptable salt of any compound of the foregoing formulas. In this aspect, any of the compounds of any of Formulas I-IV may be combined with a pharmaceutically acceptable carrier.

Salts of the compounds of the present disclosure may be made by methods known to a person skilled in the art. The acid may be an inorganic acid or an organic acid. Suitable acids include, for example, hydrochloric, hydroiodic, hydrobromic, sulfuric, phosphoric, citric, acetic and formic acids.

A variety of administration techniques may be utilized, among them oral, transdermal or parenteral techniques such as subcutaneous, intravenous, intraperitoneal, intracerebral and intracerebroventricular injections, catheterizations and the like. Such methods of administration are well-known to those skilled in the art. For a general discussion of drug delivery systems and administration modalities, see Kirk-Othmer Encyclopedia of Chemical Technology, Fourth Edition, Volume 8, pp. 445-475.

Average quantities of the compounds may vary in accordance with the binding properties of the compound (i.e., affinity, onset and duration of binding) and in particular should be based upon the recommendations and prescription of a qualified physician.

The therapeutic compositions useful in practicing the therapeutic methods of this disclosure may include, in admixture, a pharmaceutically acceptable excipient (carrier) and one or more of the compounds of the invention, as described herein as an active ingredient.

The compounds of the present invention may be administered by a variety of methods. Thus, those products of the invention that are active by the oral route may be administered in solutions, suspensions, emulsions, tablets, including sublingual and intrabuccal tablets, soft gelatin capsules, including solutions used in soft gelatin capsules, aqueous or oil suspensions, emulsions, pills, lozenges, troches, tablets, syrups or elixirs and the like. Products of the invention active on parenteral administration may be administered by depot injection, implants including Silastic™ and biodegradable implants, skin patches, skin creams, or intramuscular and intravenous injections.

Compositions may be prepared according to any method known to the art for the manufacture of pharmaceutical compositions and such compositions may contain one or more agents selected from the group consisting of sweetening agents, flavoring agents, coloring agents and preserving agents. Tablets containing the active ingredient in admixture with nontoxic pharmaceutically acceptable excipients which are suitable for manufacture of tablets are acceptable. These excipients may be, for example, inert diluents, such as calcium carbonate, sodium carbonate, lactose, calcium phosphate or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol (e.g., polyoxyethylene sorbitol mono-oleate), or a condensation product of ethylene oxide with a partial ester derived from a fatty acid and a hexitol anhydride (e.g., polyoxyethylenesorbitan mono-oleate). The aqueous suspension may also contain one or more preservatives such as ethyl or n-propyl p-hydroxybenzoate, one or more coloring agents, one or more flavoring agents and one or more sweetening agents, such as sucrose, aspartame or saccharin. Ophthalmic formulations, as is known in the art, will be adjusted for osmotic pressure.

Oil suspensions may be formulated by suspending the active ingredient in a vegetable oil, such as arachis oil, olive oil, sesame oil or coconut oil, or in a mineral oil such as liquid paraffin. The oil suspensions may contain a thickening agent, such as beeswax, hard paraffin or cetyl alcohol. Sweetening agents may be added to provide a palatable oral preparation. These compositions may be preserved by the addition of an antioxidant such as ascorbic acid.

Dispersible powders and granules of the invention suitable for preparation of an aqueous suspension by the addition of water may be formulated from the active ingredients in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, may also be present.

The pharmaceutical composition of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally occurring gums, such as gum acacia and gum tragacanth, naturally occurring phosphatides, such as soybean lecithin, esters or partial esters derived from fatty acids and hexitolamhydrides, such as sorbitan mono-oleate, and condensation products of these partial esters with ethylene oxide, such as polyoxyethylenesorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a nontoxic parenterally acceptable diluent or solvent, such as a solution of 1,3-butanediol. Among the acceptable vehicles and solvents that may be employed are water and Ringer's solution, an isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Sterilization may be performed by conventional methods known to those of ordinary skill in the art such as, for example, by aseptic filtration, or irradiation.

Aqueous formulations (i.e oil-in-water emulsions, syrups, elixirs and injectable preparations) may be formulated to achieve the pH of optimum stability. The determination of the optimum pH may be performed by conventional methods known to those of ordinary skill in the art. Suitable buffers may also be used to maintain the pH of the formulation.

The compounds of this invention may also be administered in the form of suppositories for rectal administration of the drug. These compositions can be prepared by mixing the drug with a suitable nonirritating excipient which is solid at ordinary temperatures but liquid at rectal temperatures and will therefore melt in the rectum to release the drug. Non-limiting examples of such materials are cocoa butter and polyethylene glycols.

They may also be administered by intranasal, intraocular, intravaginal, and intrarectal routes including suppositories, insufflation, powders and aerosol formulations.

Products of the invention which are preferably administered by the topical route may be administered as applicator sticks, solutions, suspensions, emulsions, gels, creams, ointments, pastes, jellies, paints, powders, and aerosols.

The advantages and features of the disclosure are further illustrated with reference to the following example, which is not to be construed as in any way limiting the scope of the disclosure but rather as illustrative of one embodiment of the disclosure in a specific application thereof.

EXAMPLES

General Peptide Synthesis Procedure

The FOCUS XC (AAPPTEC, Louisville, Ky.) automatic solid phase peptide synthesizer was used to synthesize all peptides. Reagents for the peptide synthesis were purchased from Advanced ChemTech (Louisville, Ky.), Chem-Impex International (Wood Dale, Ill.), and NovaBiochem (La Jolla, Calif.). Natural 9-Fluorenylmethoxycarbonyl(Fmoc)-amino acids with standard side-chain protecting groups were from AAPPTEC unless otherwise described. Coupling reagents O-benzotriazole-N,N,N',N'-tetramethyluroniumhexafluorophosphate (HBTU), and N-hydroxybenzotriazole (HOBt) were purchased from Chem-Impex.

Peptide acids were synthesized on preloaded Wang-resin purchased from Chem-Impex International (Wood Dale, Ill.) and peptide amides were synthesized on preloaded Rinkamide resin from Chem-Impex. Peptide synthesis follows standard solid phase peptide synthesis (SPPS) using Fmoc/HBTU chemistry (Merrifield, R. B., (1963), J. Am. Chem. Soc., 85, 2149-2154; Fields, C. G., Lloyd, D. H., Macdonald, R. L., Otteson, K. M., Noble, R. L., (1991), Pept. Res., 4, 95-101.). Crude peptides were purified on an Agilient HPLC system equipped with Prostar 210 dual pumps, a Prostar 335 Diode UV detector and a SEDEX75 (SEDERE, Olivet, France) ELSD detector. The HPLC solvent system was binary, water containing 0.1% trifluoroacetic acid (TFA) and acetonitrile containing 0.1% TFA. A linear gradient of 5%-45% acetonitrile over 20 min was used to isolate pure peptides. A Spirit™ peptide reverse phase semi-prep column 120 C18 5 μm 25×2.12 column (AAPPTec, Louisville, Ky.) was used to purify peptides. The pure peak corresponding to the correct mass of the peptide was collected and the remaining HPLC solvent was removed under a stream of nitrogen. The purity of all peptides was analyzed using an analytical Spirit™ peptide 120 C18 5 μm 25×0.46 column (AAPPTec) with a gradient of 5%-60% acetonitrile over 30 min. The molecular ion of each peptide was determined using a PE Sciex API 150 EX LC/MS system from Perkin Elmer (San Jose, Calif.).

As a general procedure, each peptide was synthesized using 100 mg solid phase resin (0.5 mmol/g) to afford 25 mg of crude peptide. For each coupling cycle, removal of Fmoc group was realized by treatment of the solid phase resin with 20% piperidine indimethylformamide. An in-line UV monitor coupled to the FOCUS XC synthesizer was used to monitor completion of the Fmoc removal step. After extensive washing with dimethylformamide and dichloromethane, 5 equivalents of Fmoc-amino acid, 5 equivalents of HBTU/HOBt and 10 equivalents of diisopropylethylamine (DIPEA) were mixed and preactivated for 2 min before loading onto the resin. Each reaction cycle took one hour to complete with constant mechanic mixing. After the last amino acid coupling cycle, the resin was treated with 20% piperidine in dimethylformamide to remove the N-terminal Fmoc group and was left as the free amine or capped with acetic or benzoic acid as designed. The cleavage of peptides from the solid phase resin was facilitated by 95/2.5/2.5 TFA/triisopropylsilane (TIS)/water treatment for 2 h at room temperature. The cleavage mixture was filtered through a glass pipette filled with cotton. The filtrate was dried under nitrogen and the crude peptides were precipitated with cold ether. After centrifugation, the peptide pellet was washed with cold ether three times and dried for downstream purification using HPLC as described above. The identity of each peptide was confirmed by ESI-MS.

Example 1: R06039-264—Formula IA

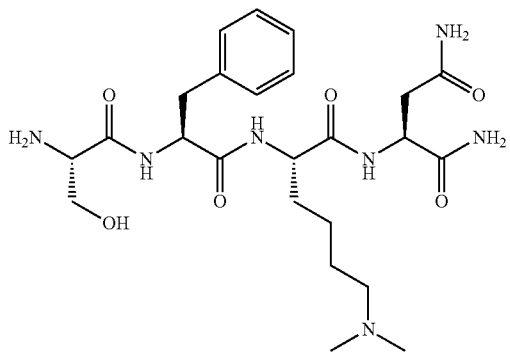 [SMILES: CN(C)CCCC[C@H](NC(=O)[C@H](Cc1ccccc1)NC(=O)[C@@H](N)CO)C(=O)N[C@@H](CC(N)=O)C(N)=O]

The peptide building block of Fmoc-Lys(Me)2-OH was purchased from Anaspec (Fremont, Calif.), Fmoc-Ser(tBu)-OH and Fmoc-Phe-OH were purchased from AAPPTEC. The preloaded solid phase support of Fmoc-Asn(Trt)-Rink amide MBHA resin (0.41 mmol/g) was purchased from Anaspec and the peptide was constructed by sequentially adding dimethyl lysine, phenylalanine, and serine to the preloaded Asn resin according to the steps described below. All building blocks were dissolved in N-methyl-2-pyrrolidone (NMP) to make a 0.25 M stock solution for use on the FOCUS peptide synthesizer. The coupling reagents HBTU and HOBt were dissolved together in dimethylformamide (DMF) at a stock concentration of 0.5 M. DIPEA was dissolved in DMF to make a 2 M stock for the reaction. Fmoc-Asn(Trt)-Rink amide resin (300 mg) was swelled in DMF for 20 min and then treated with 10 mL 20% piperidine in DMF for 5+15 min. After extensive washes with 3×DMF, 3×DCM and 3×DMF, the free amine was reacted with the appropriate Fmoc-amino acid solution (3 mL from 0.25 M stock, 5 equivalent) pre-activated with HBTU/HOBt (1.5 mL from 0.5 M stock, 5 equivalent) and DIEA (0.75 mL from 2 M stock, 10 equivalent) for 2 min. The coupling reaction time was 45 min. This cycle was repeated using until the last residue was coupled. Then the resin was then treated with piperidine to remove the terminal Fmoc group and the resin was extensively washed with DMF and DCM. The peptide was released from the resin by 6 mL TFA/triisopropylsilane (TIS)/water (95/2.5/2.5) treatment for 2 h at room temperature. The cleavage mixture was filtered through a glass pipette filled with cotton. The filtrate was dried under a stream of nitrogen and the peptide was precipitated with cold ether. After centrifugation, the peptide pellet was washed with cold ether three times and dried to result in 55 mg crude peptide. The crude peptide was subjected to semi-preparative HPLC with an isocratic 3% acetonitrile over 30 min in the previously described HPLC system. The retention time was 23.9 min. The identity of the peptide was confirmed using PESciex API 150 EX LC/MS system from Perkin Elmer.

Example 2: R06039-329 Formula IB

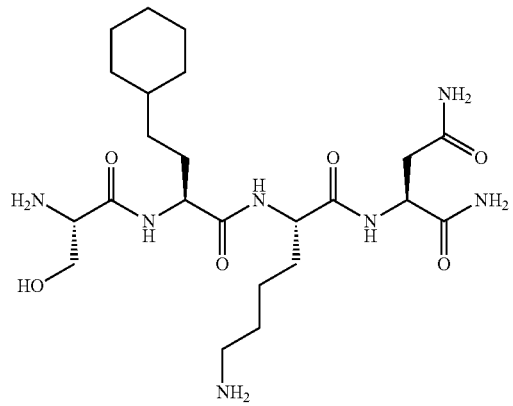 [SMILES: NCCCC[C@H](NC(=O)[C@H](CCC1CCCCC1)NC(=O)[C@@H](N)CO)C(=O)N[C@@H](CC(N)=O)C(N)=O]

The peptide building block Fmoc-HoCha-OH was purchased from Chem-Impex International. R06039-329 was synthesized and purified similarly as described for R06039-264. The retention time of R06039-329 was 11.6 min based on a linear gradient of 5%-25% acetonitrile over 20 min. The identity of the peptide was confirmed using PE Sciex API 150 EX LC/MS system from Perkin Elmer.

Example 3: R06039-351 Formula IB

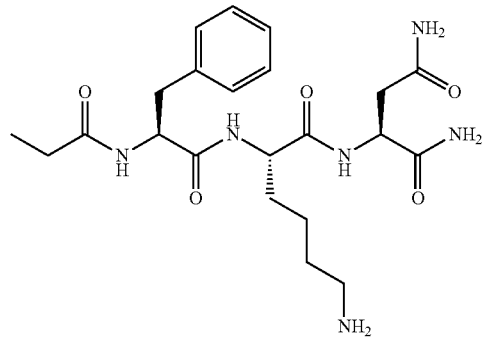 [SMILES: CCC(=O)N[C@@H](Cc1ccccc1)C(=O)N[C@@H](CCCCN)C(=O)N[C@@H](CC(N)=O)C(N)=O]

R06039-351 was synthesized similarly as described for R06039-264 except the last step. After coupling with Fmoc-Phe-OH and the removal of the terminal Fmoc group, the resin was treated with 3 mL 0.25 M propanoic acid, 1.5 mL 0.5 M HBTU/HOBt and 0.75 mL 2 M DIPEA for 30 min. After the coupling, the resin was washed and the peptide was released from the resin and purified in a similar fashion as described for R06039-264. The retention time of R06039-351 was 12.1 min based on a linear gradient of 5%-25% acetonitrile over 20 min. The identity of the peptide was confirmed using PE Sciex API 150 EX LC/MS system from Perkin Elmer.

Example 4: R06039-354 Formula IB

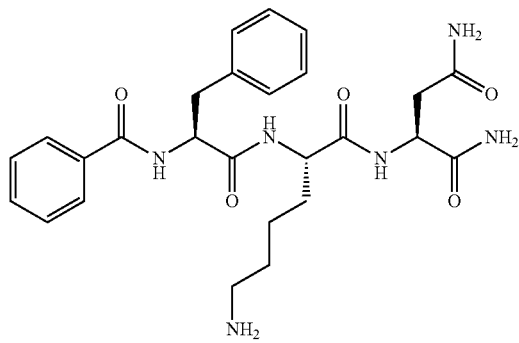 [SMILES: NCCCC[C@H](NC(=O)[C@H](Cc1ccccc1)NC(=O)c1ccccc1)C(=O)N[C@@H](CC(N)=O)C(N)=O]

R06039-354 was synthesized similarly as described for R06039-264 except the last step. After coupling with Fmoc-Phe-OH and the removal of Fmoc group, the resin was treated with 3 mL 0.25 M Benzoic acid, 1.5 mL 0.5 M HBTU/HOBt and 0.75 mL 2 MDIPEA for 30 min. After the coupling, the resin was washed and the peptide was released from the resin and purified in a similar fashion as described for R06039-264. The retention time of R06039-354 was 18.5 min based on a linear gradient of 5%-45% acetonitrile over 20 min. The identity of the peptide was confirmed using PE Sciex API 150 EX LC/MS system from Perkin Elmer.

Example 5: R06039-371 Formula IB

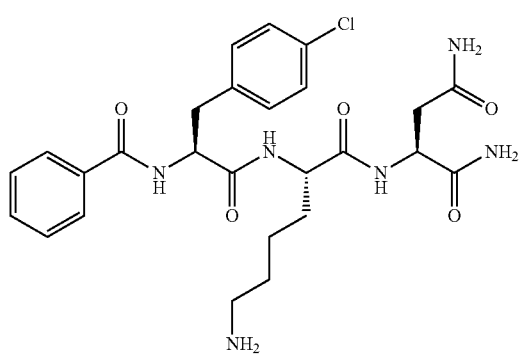 [SMILES: NCCCC[C@H](NC(=O)[C@H](Cc1ccc(Cl)cc1)NC(=O)c1ccccc1)C(=O)N[C@@H](CC(N)=O)C(N)=O]

The peptide building block of Fmoc-p-Cl-Phe-OH was purchased from Peptides International (Louisville, Ky.). The synthesis and purification procedures were similar to compound R06039-354. The retention time of R06039-371 was 20.0 min based on a linear gradient of 5%-45% acetonitrile over 20 min. And the identity of the peptide was confirmed using PE Sciex API 150 EX LC/MS system from Perkin Elmer.

Example 6: R06039-456 Formula IA

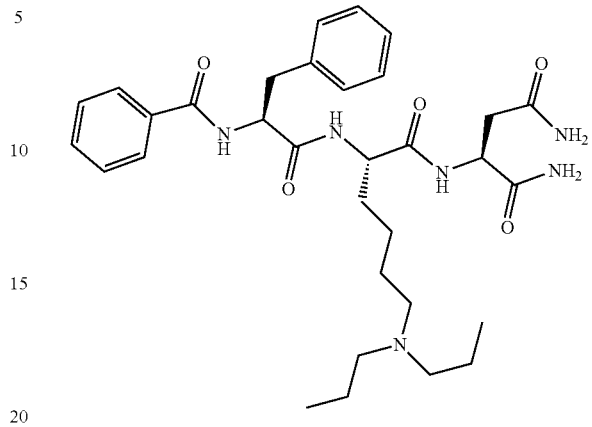

The peptide building block of Fmoc-Lys(propyl)2-OH was synthesized in house as described in procedure 1. The synthesis and purification procedures were similar to compound R06039-354. The retention time of R06039-456 was 20.4 min based on a linear gradient of 5%-95% acetonitrile over 40 min. And the identity of the peptide was confirmed using PE Sciex API 150 EX LC/MS system from Perkin Elmer.

Example 7: R06039-420 Formula IB

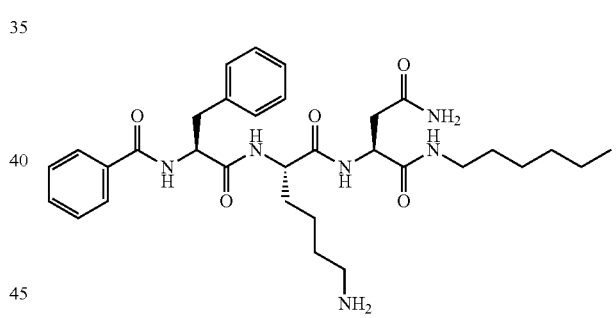

Pre-loaded Fmoc-Asn(Trt)-Wang resin (0.5 mmol/g, 200 mg) from AAPPTEC was used to synthesize R06039-420 acid (Benzoyl-Phe-Lys-Asn acid). The synthesis followed a similar strategy as described for R06039-354. The peptide acid was cleaved off the resin with the reagent cocktail containing 50% TFA and 2.5% TIS in DCM and the resin was treated for 1 h. After filtration, the filtrate containing the peptide acid was dried under a stream of nitrogen and precipitated by cold ether and washed with cold ether for three times. The crude peptide acid (45 mg) was treated with 1.0 M HCl (2 mL) and concentrated again to form the HCl salt for solution phase coupling. The crude peptide HCl salt (45 mg, 0.08 mmol) was dissolved anhydrous DMF (2 mL) and BOP (0.36 g, 0.8 mmol), and hexylamine (0.08 g, 0.8 mmol) were added. The reaction was allowed to stir at room temperature and the reaction was concentrated and injected on the HPLC system in DMSO. The purification procedures were similar to compound R06039-354. The retention time of R06039-420 was 27.7 min based on a linear gradient of 5%-95% acetonitrile over 40 min. And the identity of the peptide was confirmed using PE Sciex API 150 EX LC/MS system from Perkin Elmer.

Procedure 1

L-(S)—N,N-dipropyl-N-[(9H-fluoren-9-ylmethoxy)carbonyl]lysine

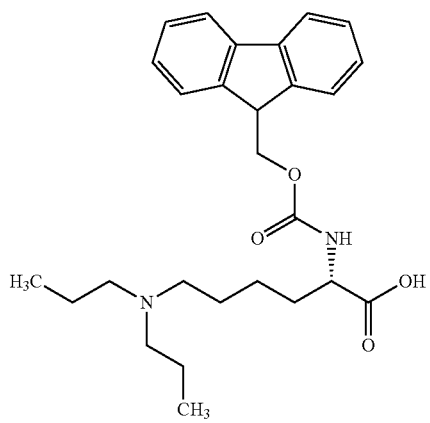

Chemical Formula: C₂₇H₃₆N₂O₄
Molecular Weight: 452.59

L-(S)—N,N-dipropyl-N-[(9H-fluoren-9-ylmethoxy)carbonyl]lysine

To a solution of L-(S)—N-[(9H-fluroen-9-ylmethoxy)carbonyl]lysine (2 g, 5.43 mmol) and propanal (664 mg, 11.43 mmol) in THF/methanol (50 mL, 4:1) was added sodium cyanoborohydride (784 mg, 12.47 mmol) in 3 portions over 2 hours. The reaction mixture was quenched after 3 hours with brine (50 mL), and the aqueous layer extracted with dichloromethane (2×50 mL). The organic layer was concentrated and purified by column chromatography (24 g, SiO₂, 0 to 50% methanol in dichloromethane) to provide L-(S)—N,N-dipropyl-N-[(9H-fluoren-9-ylmethoxy)carbonyl]lysine as a white solid (1.22 g, 49% yield). $^1$H NMR (300 MHz, CHLOROFORM-d) δ ppm 0.90-1.03 (m, 6H), 1.27-2.01 (m, 12H), 2.82-3.00 (m, 5H), 4.10-4.38 (m, 4H), 6.01-6.19 (m, 1H), 7.25-7.43 (m, 4H), 7.57-7.67 (m, 2H), 7.69-7.80 (m, 2H); MS m/z 553 (M+H)⁺, 575 (M+Na)⁺.

Procedure 2

L-(S)—N,N-dibenzyl-N-[(9H-fluoren-9-ylmethoxy)carbonyl]lysine

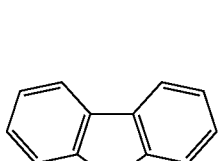

Chemical Formula: C₃₅H₃₆N₂O₄
Molecular Weight: 548.67

L-(S)—N,N-dibenzyl-N-[(9H-fluoren-9-ylmethoxy)carbonyl]lysine

To a solution of L-(S)—N-[(9H-fluroen-9-ylmethoxy)carbonyl]lysine (2 g, 5.43 mmol) and benzaldehyde (1.2 g, 11.43 mmol) in dichloromethane/THF (120 mL, 2:1) was added sodium cyanoborohydride (784 mg, 3.12 mmol) in 3 portions over 12 hours. The reaction mixture was quenched after 24 hours with brine (100 mL), and the aqueous layer extracted with dichloromethane (2×50 mL). The organic layer were concentrated and purified by column chromatography (24 g, SiO₂, 0 to 30% methanol in dichloromethane) to provide L-(S)—N,N-dibenzyl-N-[(9H-fluoren-9-ylmethoxy)carbonyl]lysine as a white solid (1.24 g, 41% yield). $^1$H NMR (300 MHz, CHLOROFORM-d) δ ppm 1.25-1.50 (m, 2H), 1.65-1.94 (m, 2H), 2.26-2.91 (m, 5H), 3.87-4.10 (m, 4H), 4.10-4.26 (m, 2H), 4.26-4.40 (m, 2H), 5.81-5.96 (m, 1H), 7.38 (br. s., 14H), 7.52-7.65 (m, 2H), 7.67-7.80 (m, 2 H); MS m/z 549 (M+H)⁺, 571 (M+Na)⁺.

Functional Determinations of EC50: Identification of functional agonists at the NPS receptor was done utilizing RD-HGA16 cells (Molecular Devices), a Chinese Hamster Ovary cell line stably expressing the promiscuous Gq-protein Gα16. RD-HGA16 cells were engineered to stably overexpress the NPS receptor. Two individual cell lines were created that stably express one of two human NPS receptor variants (NPS Ile107 and Asn107). Cells were loaded with a calcium sensitive dye (Molecular Devices) for 1 h at 370 C and compounds were assayed in separate experiments for intrinsic activity as measured by increased fluorescence intensity as a marker of mobilization of internal calcium stores using a FlexStation fluorescence plate reader. Compounds were run as 8-point full log or half log concentration curves in duplicate in order to determine the EC50 of the test compound. Each compound was tested in at least three independent experiments. A three-parameter logistic equation was fit to the concentration response data with Prism Software (v5 for Windows, GraphPad Software; San Diego, Calif.) to calculate the EC50 values. The data represent the mean±SEM from at least three independent experiments. FIG. 1 is graphical representation of the EC50 curves obtained for RO6039-351, 354 and 456.

In Vivo Studies

Male C57BL/6 mice (National Cancer Institute, Bethesda, Md., or Charles River Laboratories, Wilmington, Mass.), age 8-12 weeks, were group-housed (4 animals per cage) under controlled conditions (temperature 21 f 2° C.; relative humidity 50-60%; 12-hour light-dark cycle, lights on 6:00 AM) with free access to food and water. For intracerebroventricular (i.c.v.) drug injections, mice were briefly anesthetized with isofluorane. NPS was dissolved in phosphate-buffered saline (PBS, pH 7.4) containing 0.1% bovine serum albumin and injected i.c.v. (total volume: 2 µl) as described before (Xu et al., 2004). NPSR antagonist compounds were dissolved in PBS containing 10% Cremophor EL (Sigma) and 100 µl were injected intraperitoneally (i.p.).

Locomotion of mice was monitored in an automated activity system equipped with infrared sensors for both horizontal and vertical activity measurements (Versamax, Accuscan Inc., Columbus, Ohio). Male C57BL/6 mice were allowed to habituate to the recording chamber for 1 h. Vehicle or NPSR antagonist compound (in PBS, 10% cremophor EL) were injected i.p. 10 minutes before central administration of either NPS (1 nmole in 2 µl PBS, 0.1% BSA) or vehicle (PBS, 0.1% BSA). Recording of locomotor activity began 5 minutes after the i.c.v. injections and continued for 90 minutes. Horizontal activity represents infrared beam breaks in the X and Y dimension, while vertical activity was recorded by infrared sensors located 8 cm above the chamber floor (Z dimension). Stereotypic behavior is defined as repetitive breaks of a single beam that is not followed by a consecutive beam break of an adjacent sensor.

Figure 2:
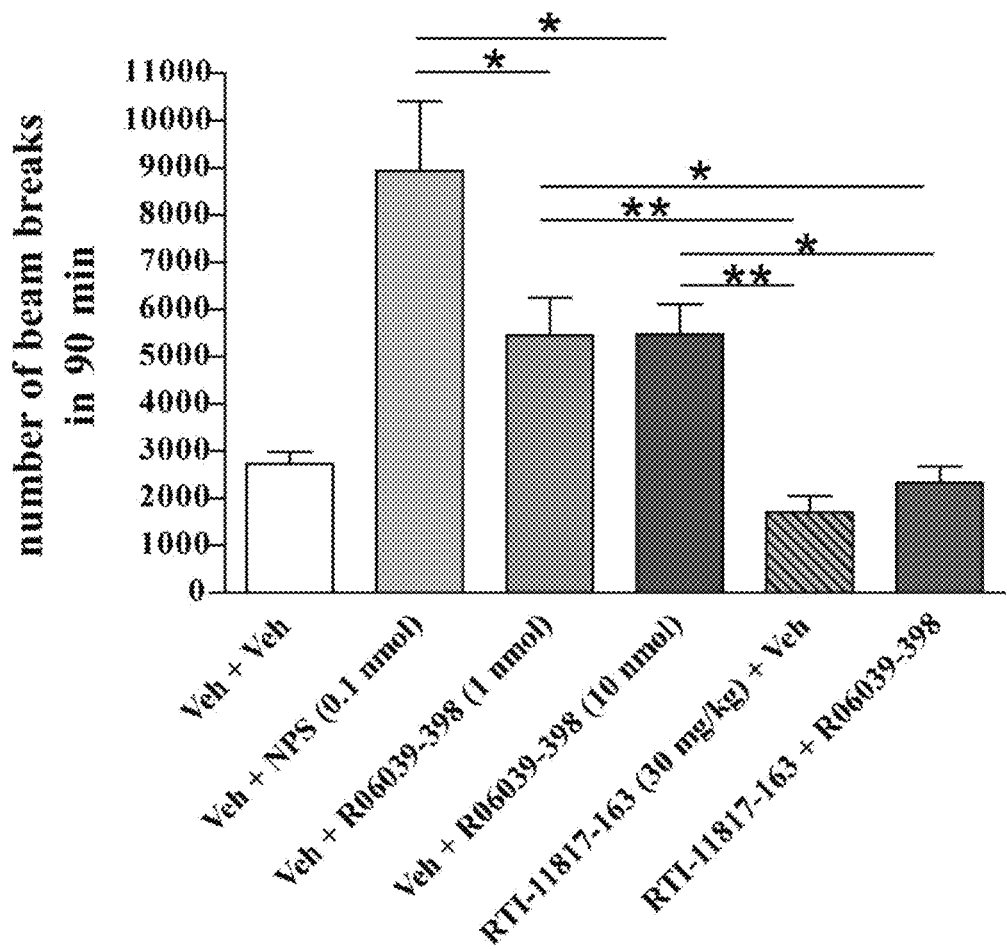
FIG. 2 is a graphical representation of the cumulative horizontal activity measured after icv administration of RO6039-398, a compound according to the present disclosure, and blockade of this activity with an NPS specific antagonist RTI-1187-163.
Figure 4:
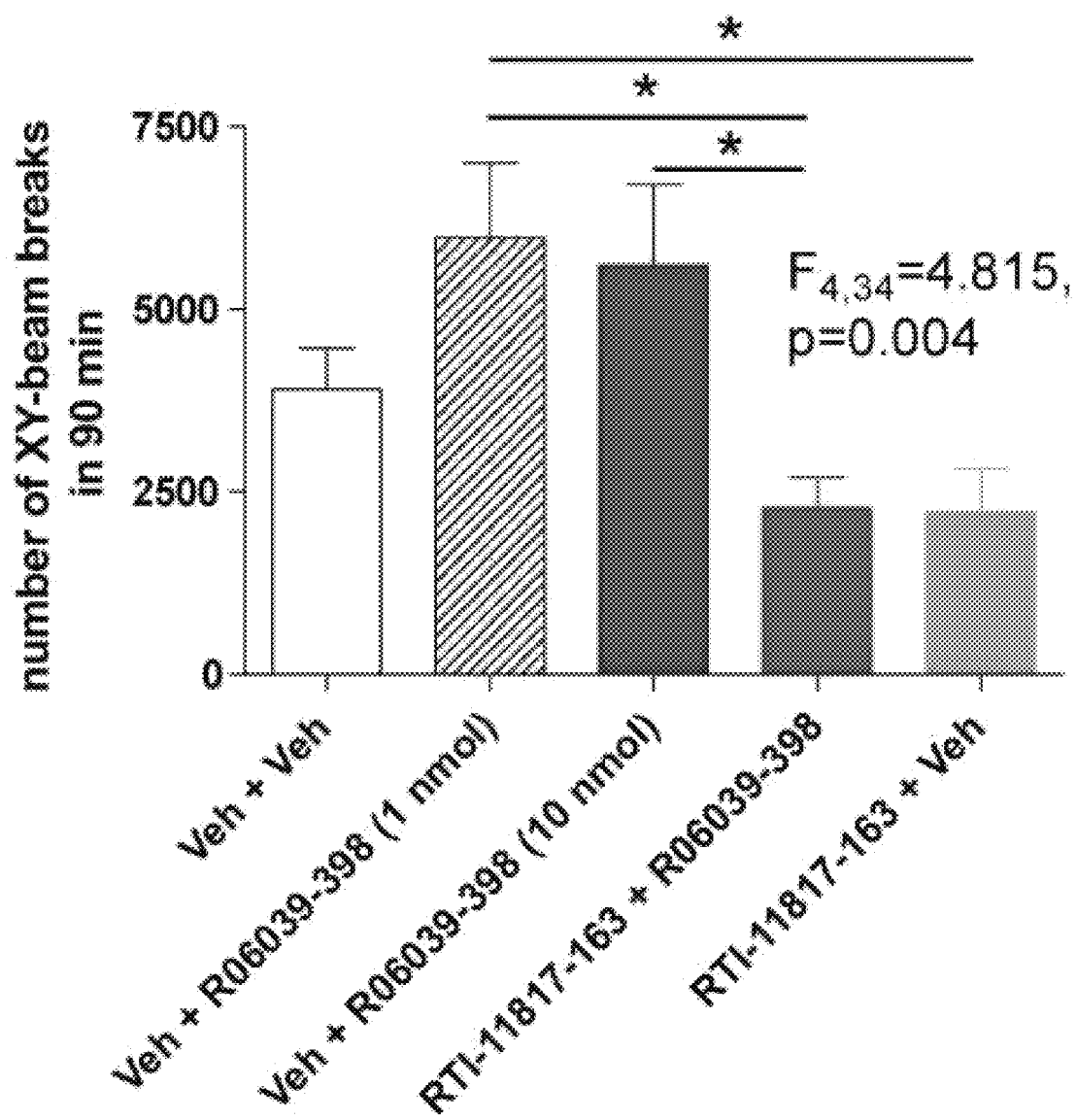
FIG. 4 is a graphical representation of the cumulative measure of horizontal behavior after icv injection of RO6039-398, a compound according to the present disclosure, and blockade of effect with an NPS specific antagonist RTI-11817-163.
Figure 5:
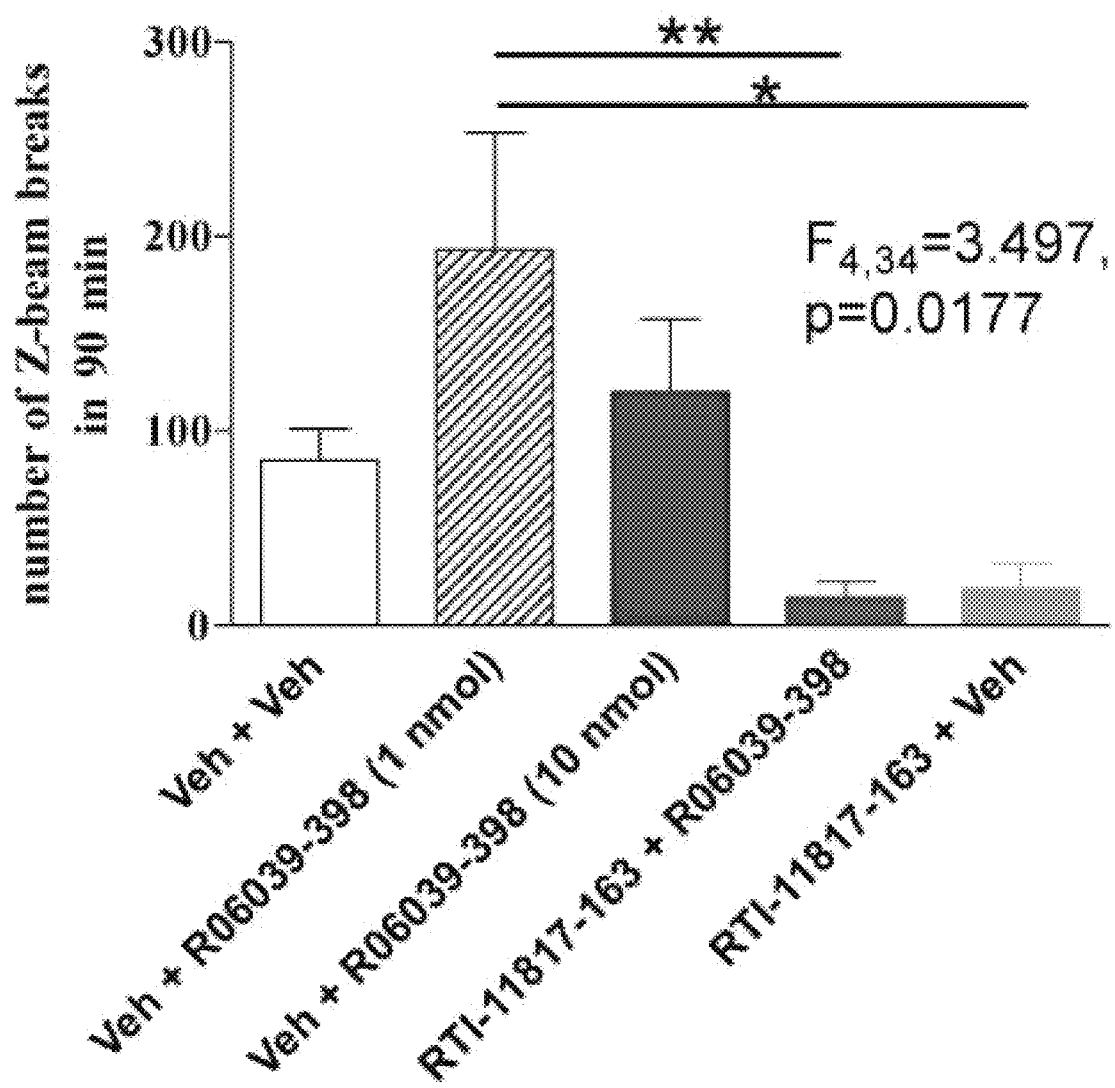
FIG. 5 is a graphical representation of the cumulative measure of vertical behavior after icv injection of RO6039-398, a compound according to the present disclosure, and blockade of effect with an NPS specific antagonist RTI-11817-163.
Figure 6:
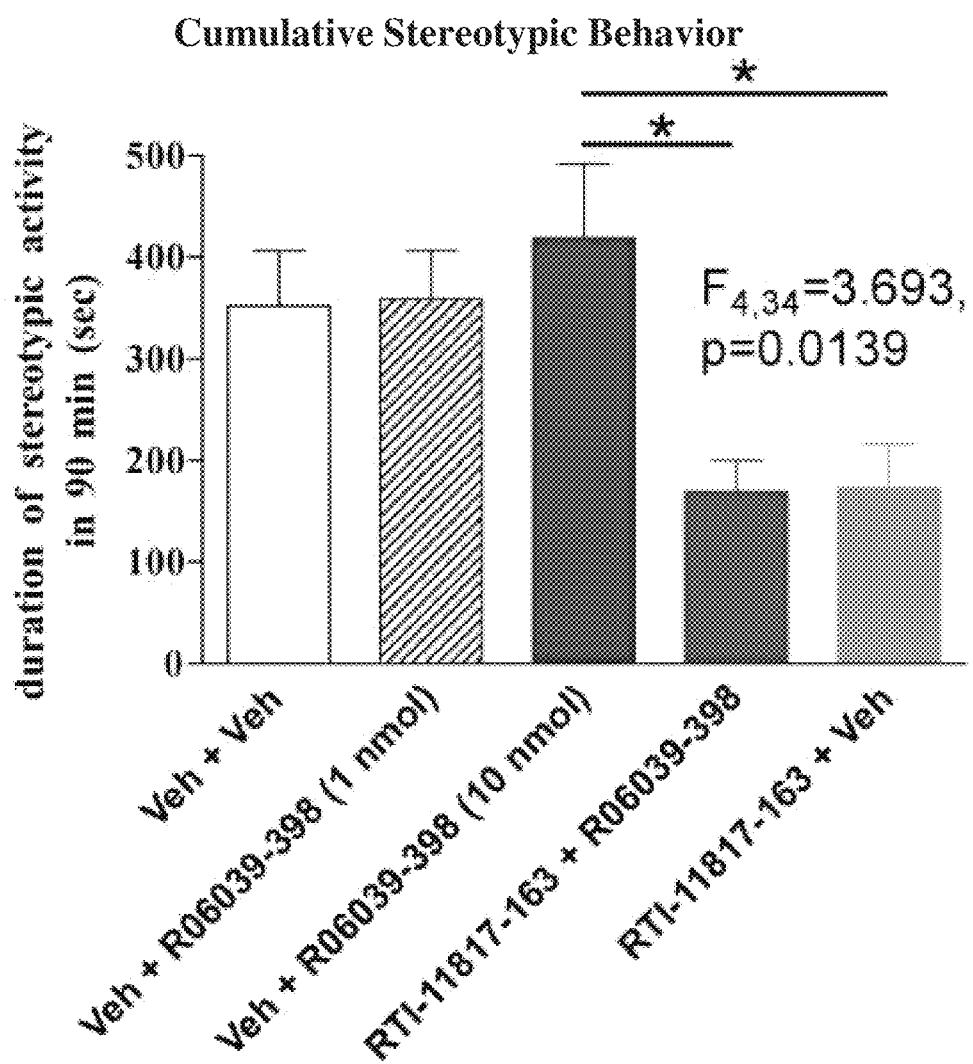
FIG. 6 is a graphical representation of the cumulative measure of stereotypic behavior after icv injection of RO6039-398, a compound according to the present disclosure, and blockade of effect with an NPS specific antagonist RTI-11817-163.

FIG. 2 illustrates the cumulative horizontal activity measured after icv administration of RO6039-398 and blockade of this activity with an NPS specific antagonist RTI-1187-163, complemented by FIG. 4 to 6 which also include vertical and stereotypic behavior. The structure of antagonist RTI-1187-163 (RO6039-229) is

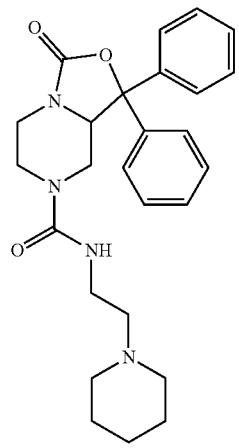 [SMILES: O=C(NCCN1CCCCC1)N1CCN2C(=O)OC(c3ccccc3)(c3ccccc3)C2C1]

(See also, table 1 Entry 11 Zhang et al. Bioorg. Med. Chem. Lett. 2008, (18), 4064). The cumulative activities measured are increasing with dose of RO6039-398. Addition of the NPS specific antagonist RTI-11817-163 reverses the agonist RO6039-398 mediated increases in horizontal and vertical activity.

Figure 3A:
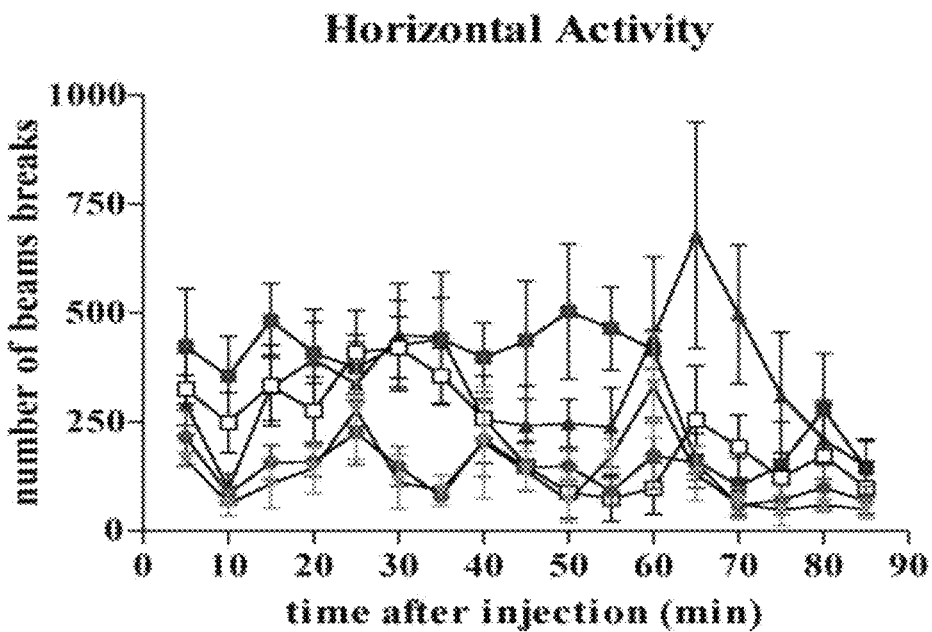
FIG. 3A is a graphical representation of the cumulative measure of horizontal behavior after icv injection of RO6039-398, a compound according to the present disclosure, and blockade of effect with an NPS specific antagonist RTI-11817-163.
Figure 3B:
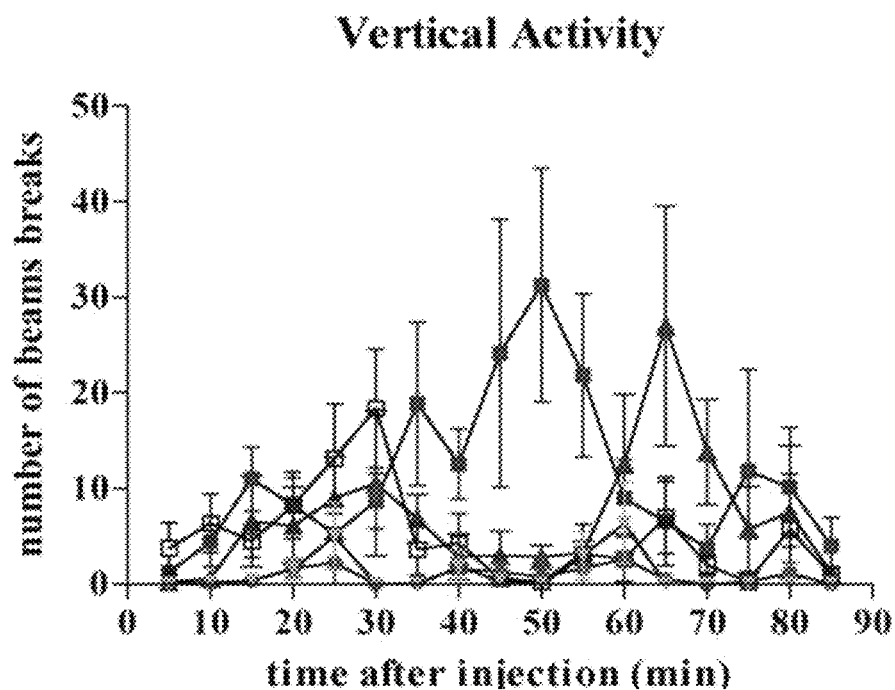
FIG. 3B is a graphical representation of the cumulative measure of vertical behavior after icv injection of RO6039-398, a compound according to the present disclosure, and blockade of effect with an NPS specific antagonist RTI-11817-163.
Figure 3C:
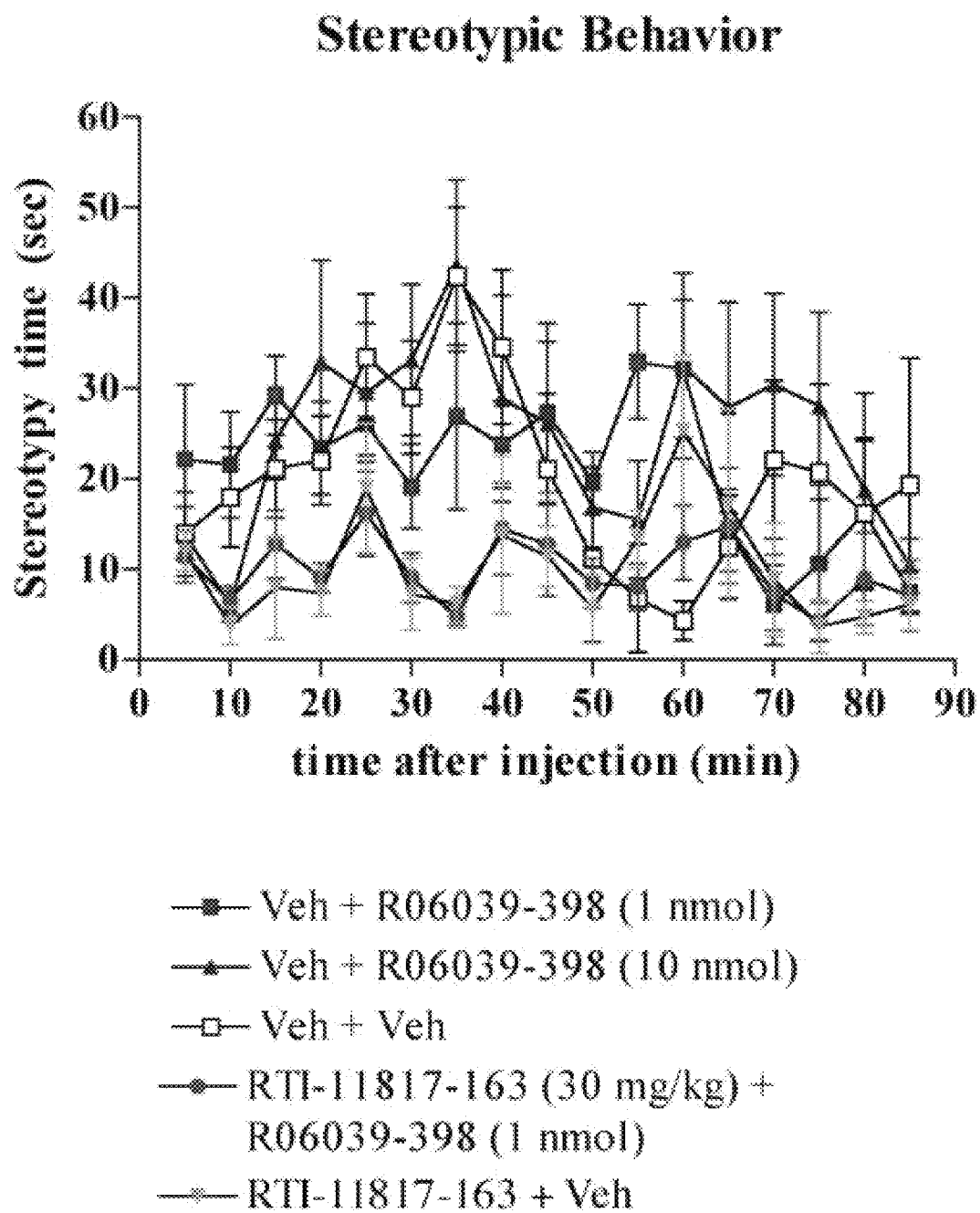
FIG. 3C is a graphical representation of the cumulative measure of stereotypic behavior after icv injection of RO6039-398, a compound according to the present disclosure, and blockade of effect with an NPS specific antagonist RTI-11817-163.

FIGS. 3A-3C illustrate the cumulative measures of horizontal, vertical and stereotypic behavior after icv injection of RO6039-398 and blockade of effect with an NPS specific antagonist RTI-11817-163.

FIGS. 4-6 illustrate the cumulative measures of horizontal, vertical and stereotypic behavior after icv injection of RO6039-398 and blockade of effect with an NPS specific antagonist RTI-11817-163.

While the disclosure has been has been described herein in reference to specific aspects, features and illustrative embodiments of the disclosure, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the subject matter as hereinafter claimed is intended to be broadly construed and interpreted, as including all such variations, modifications and alternative embodiments, within its spirit and scope.

What is claimed is:

1. A compound according to Formula (IC):

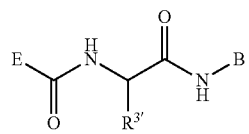

(IC)

wherein

R$^{3'}$ is H, lysine side chain, C$_1$-C$_3$ alkylated or benzylated lysine side chain, alanine side chain, unbranched C$_1$-C$_6$ alkyl, (CH$_2$)$_4$NHCOCF$_3$, or benzyl optionally substituted with nitro;

B is a five membered saturated ring substituted with one C(O)NH$_2$ group, or a six membered saturated or aromatic ring substituted with one C(O)NH$_2$ group; and E is

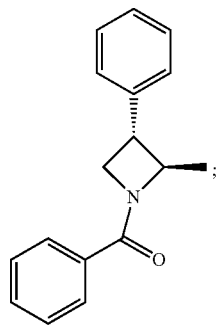 [SMILES: C[C@@H]1[C@@H](c2ccccc2)CN1C(=O)c1ccccc1]

or a pharmaceutically acceptable salt thereof.

2. The compound according to claim 1, wherein R$^{3'}$ is a lysine side chain, —(CH$_2$)$_4$—NH$_2$.

3. The compound according to claim 1, wherein B is a six membered saturated or aromatic ring substituted with one C(O)NH$_2$ group.

4. A method for treating a subject having a condition or disorder where modulation of neuropeptide S receptor activity is of therapeutic benefit, wherein such disorder or condition is selected from the group consisting of substance abuse, narcolepsy, insomnia, obesity, cognitive decline, dementia, Alzheimer's disease, panic disorder, generalized anxiety, PTSD, phobias, and schizophrenia, comprising administering to said subject having said condition or disorder a therapeutically effective amount of a compound according to claim 1.

5. The method of claim 4, further comprising administering an effective amount of a second therapeutically effective agent.

* * * * *

UNITED STATES PATENT AND TRADEMARK OFFICE
CERTIFICATE OF CORRECTION

PATENT NO. : 11,220,526 B2
APPLICATION NO. : 16/090728
DATED : January 11, 2022
INVENTOR(S) : Scott Runyon et al.

It is certified that error appears in the above-identified patent and that said Letters Patent is hereby corrected as shown below:

On the Title Page

Item (73); insert second assignee:
-- The Regents of the University of California, Oakland, California --

Signed and Sealed this
Thirtieth Day of August, 2022

Katherine Kelly Vidal
*Director of the United States Patent and Trademark Office*